United States Patent

Ishii et al.

[11] Patent Number: 5,902,240
[45] Date of Patent: May 11, 1999

[54] METHOD AND APPARATUS FOR OSTEOPOROSIS DIAGNOSIS

[75] Inventors: Tetsuya Ishii; Masashi Kuriwaki; Yasuyuki Kubota; Yuichi Nakamori, all of Kyoto, Japan

[73] Assignee: Sekisui Kagaku Kogyo Kabushiki Kaisya, Osaka, Japan

[21] Appl. No.: 08/930,998

[22] PCT Filed: Feb. 21, 1997

[86] PCT No.: PCT/JP97/00501

§ 371 Date: Oct. 21, 1997

§ 102(e) Date: Oct. 21, 1997

[87] PCT Pub. No.: WO97/30635

PCT Pub. Date: Aug. 28, 1997

[30] Foreign Application Priority Data

Feb. 21, 1996 [JP] Japan ................................. 8/34100

[51] Int. Cl.[6] .................................................. A61B 8/00
[52] U.S. Cl. ............................................................. 600/438
[58] Field of Search ................................ 600/442, 448, 600/449, 438

[56] References Cited

U.S. PATENT DOCUMENTS 4,930,511   6/1990   Rossman et al. .

FOREIGN PATENT DOCUMENTS 2-104337   of 1990   Japan .

Primary Examiner—Francis J. Jaworski
Assistant Examiner—Maulin Patel
Attorney, Agent, or Firm—Oblon, Spivak, McClelland, Maier & Neustadt, P.C.

[57] ABSTRACT

An osteoporosis diagnosis yapparatus provided with a two-dimensional ultrasonic transducer array (3) comprising a number of cells ($1_1$, $1_2$, . . . ). The ultrasonic transducer array (3) is applied to the skin covering a predetermined bone of a subject, and the individual cells sequentially emit a predetermined number of ultrasonic pulses through the skin while receiving echoes from the bone. The received echo data are processed so that they can be handled in a plane-wave problem, from which the information on the reflection from the bone is determined. This information is processed to obtain the acoustic impedance of a cortical bone and a cancellous bone, so as to check for the presence of osteoporosis. The information on the reflection from the bone can also be handled as an eigen-value problem, and, when the information is handled in such a manner, the shape determination of a bone becomes un necessary.

21 Claims, 9 Drawing Sheets

3; ULTRASONIC TRANSDUCER ARRAY

FIG.8

METHOD AND APPARATUS FOR OSTEOPOROSIS DIAGNOSIS

TECHNICAL FIELD

This invention relates to an ultrasonic pulse-echo type osteoporosis diagnosing apparatus and method, which diagnoses osteoporosis by emitting ultrasonic pulses towards a certain bone of an examinee and detecting the echoes from the bone.

BACKGROUND ART

With the emergence of a more aged society in recent years, the bone disease termed osteoporosis has been becoming a problem. In this disease the calcium is withdrawn from the bones leaving them friable and prone to fracture at the slightest impact; and it is one motive for concern in old people. Physical diagnosis is performed mainly by determining the density of bone precisely by means of diagnostic apparatus employing X-rays, typified by DXA and DCT; however, physical diagnosis by means of X-rays is beset by various problems such as the fact that the apparatus is large, and that its use is restricted by the need to prevent harmful radiation exposure.

Accordingly, diagnostic apparatus employing ultrasound has started to become popular because the equipment is simple and does not cause such problems. Diagnostic apparatus employing ultrasound measures the speed and attenuation of ultrasound waves propagated inside bony tissues, and uses this to estimate the density and elastic modulus (elastic strength) of the bone. If a low estimated value is obtained it can be deduced that this is because of withdrawal of calcium from the bone, and hence osteoporosis is diagnosed.

For example, in the diagnostic apparatus recorded in Japanese Laid-Open Patent Application No. H2-104337 (U.S patent application No. 193,295) the speed of sound in bony tissue is measured by placing two ultrasonic transducers facing each other on either side of the bony tissue of an examinee chosen as the measurement site, emitting ultrasonic pulses towards the bony tissue from an ultrasound transducer on one side and receiving the ultrasonic pulses transmitted by the bone tissue at the ultrasound transducer on the other side, in order to determine the speed of sound within the bone; and progress in osteoporosis is diagnosed when the speed of sound inside the bony tissue is slow. This is because the data processing algorithm of this diagnostic apparatus is based on the working premise that the speed of sound in bony tissue is proportional to bone density.

However, there is no firmly established theoretical basis for linking bone density and the speed of sound: strictly speaking the speed of sound in bony tissue is not proportional to bone density, but is given by the square root of "the elastic modulus of the bone/bone density". And since the elastic modulus of bone rises as bone density increases, and therefore the modulus of elasticity of bone and bone density contribute to the speed of sound in such a way that they cancel one another out, the speed of sound in bony tissue cannot respond sensitively to an increase in bone density, and the coefficient of correlation between the speed of sound in bony tissue on the one hand and bone density on the other is not at all high. There is also no established theoretical basis for linking bone density and attenuation of ultrasound waves.

Therefore, it is unreasonable to expect highly reliable diagnoses from prior diagnostic apparatus which estimate bone density and the elastic modulus of bone on the basis if results of determination of attenuation of ultrasound waves, or determination of the speed of sound in bony tissue.

As means of overcoming these inadequacies, Japanese Patent Applications No. H6-310445, No. H7-140730 and No. H7-140734, applied for by the present applicant, propose ultrasonic pulse-echo type apparatus for diagnosing osteoporosis in which a single ultrasonic transducer is used; ultrasonic pulses are emitted repeatedly towards smooth-surfaced bony tissue; the echoes returned from the bony tissue are received; the maximum echo (which can be regarded to be the echo due to perpendicular reflection) is extracted from the echoes received; the reflection coefficient and acoustic impedance, etc., of the bone are calculated from the maximum echo extracted, and the calculated values are used as the basis for diagnosing osteoporosis.

However, although it is possible, with the ultrasonic pulse-echo type apparatus for diagnosing osteoporosis claimed in the applications mentioned above, to emit adequate planewave ultrasonic pulses towards smooth-surfaced bony tissue and to receive back perpendicularly reflected echoes when the transducer is in contact with the skin of the examinee, there is the problem that the procedure is complex, because the direction of the transducer has to be altered in order to locate the maximum echo, and this requires skill and effort on the part of the person carrying out the procedure.

This invention is a response to the situation above, and its object is to offer an apparatus for diagnosing osteoporosis and a method for diagnosing osteoporosis which can give highly reliable diagnoses, by using a simple procedure which does not involve exposure to radiation.

DISCLOSURE OF THE INVENTION

In the apparatus (and method) for diagnosing osteoporosis of this invention repeatedly emits ultrasonic pulses towards the bone of the examinee, the echo waves returned from the bone each time are received, and the echo data which is received is used as the basis for diagnosing osteoporosis.

Therefore, according to a 1st viewpoint of the present invention, an apparatus for diagnosing osteoporosis is offered which is provided with an ultrasonic transducer array comprising a 2-dimensional arrangement or 1-dimensional arrangement of N ultrasonic transducer elements (N is a natural number$\geq 2$), and means for transmitting and receiving ultrasonic waves, connected to each of the ultrasonic transducer elements above, and an A/D converter which digitalizes signals received from each of the ultrasonic transducer elements above, and means for determining echo waveforms, which determines the waveforms $S_{ij}(t)$ of echoes received by the ith ultrasonic transducer elements of the N ultrasonic transducers above from the bone due to the emission of ultrasonic pulses from the jth ultrasonic transducer elements, and means for constructing a scattering matrix, which performs the necessary combination of these measurements to find the N×N scattering matrix $[S_{ij}(t)]$, and a Fourier transformation means which subjects the scattering matrix $[S_{ij}(t)]$ to Fourier transformation with time, and means for calculating wave reflection information, which calculates information on-wave reflection by the bone of the examinee on the basis of the Fourier transformed scattering matrix $[S_{ij}(\omega)]$.

In a preferred form of the scattering matrix construction means, the number of necessary combinations of ith ultrasonic transducer element and jth ultrasonic transducer element is within the range $N(N+1)/2$ to $N \times N$.

In addition, in the Fourier transformation means above, Fourier transformation is preferably performed, following the processing algorithm, by applying a gate to the waveform considered to be the echo received from the bone.

According to the 2nd viewpoint of this invention, an apparatus for diagnosing osteoporosis is offered which is provided with an ultrasonic transducer array comprising a 2-dimensional arrangement or 1-dimensional arrangement of N ultrasonic transducer elements (N is a natural number$\geq 2$), and means for transmitting and receiving ultrasonic waves, connected to each of the ultrasonic transducer elements above, and an, A/D converter which digitalizes signals received from each of the ultrasonic transducer elements above, and means for determining echo waveforms which determines the waveforms $S_{ij}$ (t) of echoes received by the ith ultrasonic transducer elements of the N ultrasonic transducers above from the bone due to the emission of elements, and means for constructing a scattering matrix, which performs the necessary combinations of these measurements to find an N×N scattering matrix $[S_{ij}$ (t)], and Fourier transformation means which subjects the scattering matrix $[S_{ij}$ (t)] to Fourier transformation with time, and means for calculating wave reflection information, which calculates information on wave reflection by the bone of the examinee on the basis of the Fourier transformed scattering matrix $[S_{ij}$ ($\omega$)],
in which the aforementioned means for calculating wave reflection information is characterized in that, following a processing algorithm, it finds a single value or plurality of values for $\lambda$, counting from the largest absolute value for $\lambda$ among the values for $\lambda$ established by Equation (7), and calculates information on wave reflection by the bone of the examinee on the basis of the value(s) of $\lambda$ that are found.

$$\sum_j S_{ij}(\omega)\Psi_j(\omega) = \lambda\Psi_i^*(\omega) \qquad (7)$$

According to the 3rd viewpoint of this invention, an apparatus for diagnosing osteoporosis is offered which is provided with an ultrasonic transducer array comprising a 2-dimensional arrangement or 1-dimensional arrangement of N ultrasonic transducer elements (N is a natural number$\geq 2$), and means for transmitting and receiving ultrasonic waves, connected to each of the ultrasonic transducer elements above, and an A/D converter which digitalizes signals received from each of the ultrasonic transducer elements above, and means for determining echo waveforms, which determines the waveforms $S_{ij}$ (t) of echoes received by the ith ultrasonic transducer elements of the N ultrasonic transducers above from the bone due to the emission of ultrasonic pulses from the jth ultrasonic transducer elements, and means for constructing a scattering matrix, which performs the necessary combination of these measurements to find an N×N scattering matrix $[S_{ij}$ (t)], and Fourier transformation means which subjects the scattering matrix $[S_{ij}$ (t)] to Fourier transformation with time, and means for calculating wave reflection information, which calculates information on wave reflection by the bone of the examinee on the basis of the Fourier transformed scattering matrix $[S_{ij}$ ($\omega$)], in which the aforementioned reflected wave information calculating means, following a processing algorithm, finds a single eigenvalue $\lambda$ or a plurality of eigenvalues for $\lambda$, counting from the largest absolute value for $\lambda$ among the eigenvalues for $\lambda$ established by equation (8), and calculates information on wave reflection by the bone of the examinee on the basis of the eigenvalue(s) of $\lambda$ that are found. The preferred form in this case is to multiply the eigenvalue(s) $\lambda$ by a proportionality constant so as to find the reflection coefficient of the bone.

$$\begin{bmatrix} Re(S(\omega)) - Im(S(\omega)) \\ -Im(S(\omega)) - Re(S(\omega)) \end{bmatrix} \begin{bmatrix} Re(\vec{\Psi}_{in}(\omega)) \\ Im(\vec{\Psi}_{in}(\omega)) \end{bmatrix} = \lambda \begin{bmatrix} Re(\vec{\Psi}_{in}(\omega)) \\ Im(\vec{\Psi}_{in}(\omega)) \end{bmatrix} \qquad (8)$$

$\lambda$ is eigenvalues for the N×N real symmetrical matrix $$\begin{bmatrix} Re\,S(\omega) & -Im\,S(\omega) \\ -Im\,S(\omega) & -Re\,S(\omega) \end{bmatrix}.$$

According to the 4th viewpoint of this invention, an apparatus for diagnosing osteoporosis is offered which is provided with an ultrasonic transducer array comprising a 2-dimensional arrangement or 1-dimensional arrangement of N ultrasonic transducer elements (N is a natural number$\geq 2$), and means for transmitting and receiving ultrasonic waves, connected to each of the ultrasonic transducer elements above, and an A/D converter which digitalizes signals received from each of the ultrasonic transducer elements above, and means for determining echo waveforms, which determines the waveforms $S_{ij}$ (t) of echoes received by the ith ultrasonic transducer elements of the N ultrasonic transducers above from the bone due to the emission of ultrasonic pulses from the jth ultrasonic transducer elements, and means for constructing a scattering matrix, which performs the necessary combination of these measurement to find an N×N scattering matrix $[S_{ij}$ (t)], and Fourier transformation means which subjects the scattering matrix $[S_{ij}$ (t)] to Fourier transformation with time, and means for calculating wave reflection information, which calculates information on wave reflection by the bone of the examinee on the basis of the Fourier transformed scattering matrix $[S_{ij}$ ($\omega$)], in which the the aforementioned means for calculating wave reflection information is characterized in that, following a processing algorithm, it finds the coordinates of N bone elements in the subject (the same number as the number of ultrasonic transducer elements above) on the basis of the waveforms $S_{ij}$ (t) of the echoes received above, processes the data in order to reduce wave reflection from the predetermined shape to a planewave problem, taking into account the retardation in propagation of the respective received echoes, and calculates information on wave reflection by the bone above after reducing it to a planewave problem.

In the preferred form of the above means for calculating wave reflection information, information on bone wave reflection from cortical bone to soft tissues and information on bone wave reflection from cancellous bone to cortical bone is included in calculating information on wave reflection from the bone above.

The acoustic impedance of the bone above, or the acoustic impedance of the cortical bone and the acoustic impedance of the cancellous bone, are also preferably calculated on the basis of the bone wave reflection information above.

According to the 5th viewpoint of this invention, an apparatus for diagnosing osteoporosis is offered which is a device for diagnosing osteoporosis in which a predetermined number of ultrasonic pulses are emitted in sequence, one by one from each of the ultrasonic transducer elements of an array of ultrasonic transducers comprising a plurality of ultrasonic transducer elements arranged in 2 dimensions or 1 dimension, in contact with the surface of the skin of the examinee covering a predetermined bone, in the direction of a predetermined area of the above bone, and the echoes generated from the above bone for each pulse that is emitted are received by the each of the ultrasonic transducer elements above, and osteoporosis is diagnosed by predetermined analysis of predetermined received signals after converting the latter into digital echo signals by means of an analogue/digital converter, which is capable of outputting from the plurality of ultrasonic transducer elements above ultrasonic waves of a waveform represented by Equation (9), towards the predetermined area of the bone above which is the site of measurement.

$$\begin{bmatrix} a_{1(t)} \\ \vdots \\ a_{N(t)} \end{bmatrix} = F^{-1} \left[ T_{(\omega)}^{-1} \begin{bmatrix} 1 \\ \vdots \\ 1 \end{bmatrix} \right] \quad (9)$$

Where $a_1, a_2, \ldots, a_N$ are the incident waves from the 1st, 2nd, ..., Nth ultrasonic transducer element, $F^{-1}$ represents a inverse Fourier transformation, $T(\omega)^{-1}$ is an inverse matrix of the matrix $T(\omega)$ in which the elements are Green functions including as variables the distances from given bone elements to given ultrasonic transducer elements.

The preferred forms of the 1st to 5th viewpoints of this invention offer apparatuses for diagnosing osteoporosis in which this apparatus for diagnosing osteoporosis is provided with a pulse generating means which generates electric pulses repeatedly in a predetermined cycle, and an output switching means in order to enable any 1 selected ultrasonic transducer element to be connected 1-1 to the pulse generating means above, and to be able to switch the connection, and an input switching means in order to enable any 1 selected ultrasonic transducer element above to be connected 1-1 to the analogue/digital converter above, and to be able to switch the connections, and a control means which controls the output switching means above so that electrical pulses produced in the pulse generating means above are distributed in sequence to each of the ultrasonic transducer elements above, and controls the input switching means above so that the received signals output from each of the ultrasonic transducer elements above are introduced in sequence to the analogue/digital converter above.

Also in a preferred form of the 1th to 5th viewpoints of this invention, in this apparatus for diagnosing osteoporosis the control means above controls the output switching means so that electrical pulses are distributed at least N at a time to each of the ultrasonic transducer elements, and controls the input switching means above, in relation to the N echoes from the bone generated for the N ultrasonic pulses emitted in sequence from the same ultrasonic transducer elements above, so that each echo signal received from mutually different ultrasonic transducer elements is extracted in sequence and introduced to the analogue/digital converter.

In another preferred form of the 1th to 5th viewpoints of this invention, an apparatus for diagnosing osteoporosis is. offered which is provided with an ultrasonic transducer array which has in all A×B cells divided into B groups with A cells in each group (A and B being natural numbers $\geq 2$), and a pulse generating means which generates electrical pulses repeatedly in a predetermined cycle, and B analogue/digital converters above corresponding to each of the blocks, and an output switching means in order to enable any 1 selected ultrasonic transducer element above to be connected 1-1 to the pulse generating means above, and to be able to switch the connection, and an input switching means in order to enable any 1 selected ultrasonic transducer element above in each group to be connected 1-1 to the analogue/digital converter above, and to be able to switch the connections, and a control means which controls the output switching means so that electrical pulses are distributed at least A at a time to each of the aforementioned ultrasonic transducer elements, and also controls the input switching means above in relation to the A echoes from the bone generated in response to A ultrasonic pulses emitted in sequence from the same ultrasonic transducer elements above, so that each echo signal received from mutually different ultrasonic transducer elements above in each group are sequentially extracted and introduced to the corresponding analogue/digital converter above.

In a further preferred form of the 1th to 5th viewpoints of this invention, an apparatus for diagnosing osteoporosis is offered which is provided with a plurality of analogue/digital converters, connected 1-1 to each of the ultrasonic transducer elements above, and a pulse generating means which generates electrical pulses repeatedly in a predetermined cycle, and an output switching means in order to enable the selection or switching of any of the ultrasonic transducer elements above connected 1-1 to the the aforementioned pulse generating means, and a control means which controls the aforementioned output control means so that electrical pulses produced in the pulse generating means above are fed in sequence to each of the ultrasonic transducer elements above.

In yet another preferred form of the 1th to 5th viewpoints of this invention, an apparatus for diagnosing osteoporosis is offered in which this apparatus for diagnosing osteoporosis is provided with a plurality of analogue/digital converters above, connected 1-1 to each of the ultrasonic transducer elements above, and a plurality of pulse generating means, connected 1-1 to each of the ultrasonic transducer elements above, and a control means which controls the sequence of the different pulse generating means above so that electrical pulses are fed in sequence to each of the ultrasonic transducer elements above.

A 6th viewpoint of the present invention offers a method for diagnosing osteoporosis which uses an ultrasonic transducer array comprising a 2-dimensional or 1-dimensional arrangement of N ultrasonic traducer elements (where N is a natural number $\geq 2$), and ultrasonic signal transmitting and receiving means connected to each of the ultrasonic transducer elements above, and an analogue/digital converter which digitalizes signals received from each of the ultrasonic transducer elements above; and which determines the waveforms $S_{ij}(t)$ of echoes received by the ith ultrasonic transducer elements of the N ultrasonic transducers above from the bone due to the emission of ultrasonic pulses from the jth ultrasonic transducer elements, and performs the necessary combination of these measurements to find an N×N scattering matrix $[S_{ij}(t)]$, and subjects the scattering matrix $[S_{ij}(t)]$ found above to Fourier transformation with time, and employs the Fourier transformed N×N scattering matrix $[S_{ij}(\omega)]$ as the basis for calculating information on wave reflection by the bone of the examinee.

And a 7th viewpoint of the present invention offers a method for diagnosing osteoporosis which uses an ultrasonic transducer array comprising a 2-dimensional or 1-dimensional arrangement of N ultrasonic traducer elements (where N is a natural number $\geq 2$), and ultrasonic signal transmitting and receiving means connected to each of the ultrasonic transducer elements above, and an analogue/digital converter which digitalizes signals received from each of the ultrasonic transducer elements above; and which determines the waveforms $S_{ij}(t)$ of echoes received by the ith ultrasonic transducer elements of the N ultrasonic transducers above from the bone due to the emission of ultrasonic pulses from the jth ultrasonic transducer elements, and performs the necessary combination of these measurements to find an N×N scattering matrix $[S_{ij}(t)]$, and subjects the scattering matrix $[S_{ij}(t)]$ found above to Fourier transformation with time, and employs the Fourier transformed N×N scattering matrix [$S_{ij}(\omega)$] as the basis for calculating information on wave reflection by the bone of the examinee, and in this process finds a single value or multiple values for $\lambda$, counting from the absolute largest value of $\lambda$ established by Equation (10), and employs the value(s) of $\lambda$ that are found as the basis for calculating information on wave reflection by the bone of the examinee.

$$\sum_j S_{ij}(\omega)\Psi_j(\omega) = \lambda \Psi_i^*(\omega) \tag{10}$$

And a 8th viewpoint of the present invention offers a method for diagnosing osteoporosis which uses an ultrasonic transducer array comprising a 2-dimensional or 1-dimensional arrangement of N ultrasonic traducer elements (where N is a natural number $\geq 2$), and ultrasonic signal transmitting and receiving means connected to each of the ultrasonic transducer elements above, and an analogue/digital converter which digitalizes signals received from each of the ultrasonic transducer elements above; and which determines the waveforms $S_{ij}(t)$ of echoes received by the ith ultrasonic transducer elements of the N ultrasonic transducers above from the bone due to the emission of ultrasonic pulses from the jth ultrasonic transducer elements, and performs the necessary combination of these measurements to find an N×N scattering matrix [$S_{ij}(t)$], and subjects the scattering matrix [$S_{ij}(t)$] found above to Fourier transformation with time, and employs the Fourier transformed N×N scattering matrix [$S_{ij}(\omega)$] as the basis for calculating information on wave reflection by the bone of the examinee, and in this process finds a single eigenvalue $\lambda$ or multiple eigenvalues $\lambda$, counting from the absolute largest value of $\lambda$ established by Equation (11), and employs the eigenvalue(s) $\lambda$ that are found as the basis for calculating information on reflection by the bone of the examinee.

$$\begin{bmatrix} Re(S(\omega)) - Im(S(\omega)) \\ -Im(S(\omega)) - Re(S(\omega)) \end{bmatrix} \begin{bmatrix} Re(\vec{\Psi}_{in}(\omega)) \\ Im(\vec{\Psi}_{in}(\omega)) \end{bmatrix} = \lambda \begin{bmatrix} Re(\vec{\Psi}_{in}(\omega)) \\ Im(\vec{\Psi}_{in}(\omega)) \end{bmatrix} \tag{11}$$

$\lambda$ is eigenvalues of the N×N real symmetrical matrix $$\begin{bmatrix} Re\, S(\omega) & -Im\, S(\omega) \\ -Im\, S(\omega) & -Re\, S(\omega) \end{bmatrix}.$$

And a 9$^{th}$ viewpoint of the present invention offers a method for diagnosing osteoporosis which uses an ultrasonic transducer array comprising a 2-dimensional or 1-dimensional arrangement of N ultrasonic traducer elements (where N is a natural number $\geq 2$), and ultrasonic signal transmitting and receiving means connected to each of the ultrasonic transducer elements above, and an analogue/digital converter which digitalizes signals received from each of the ultrasonic transducer elements above; and which determines the waveforms $S_{ij}(t)$ of echoes received by the ith ultrasonic transducer elements of the N ultrasonic transducers above from the bone due to the emission of ultrasonic pulses from the jth ultrasonic transducer elements, uses the determined waveforms $S_{ij}(t)$ of the received echoes as a basis for calculating the coordinates of N bone elements in the examinee (the same number as the number of ultrasonic transducer elements above), processes the data in order to reduce wave reflection from the predetermined shape to a planewave problem, taking into account the retardation in propagation of the respective received echoes, and calculates information on wave reflection by the bone above after reducing it to a planewave problem.

A 10$^{th}$ viewpoint of this invention offers a method for diagnosing osteoporosis, which is a method for diagnosing osteoporosis in which ultrasonic pulses are emitted a predetermined number of times in sequence from each of the ultrasonic transducer elements of an ultrasonic transducer array comprising a plurality of ultrasonic transducer elements arranged in 2 dimensions or 1 dimension, in contact with the surface of the skin of the examinee covering a predetermined bone, in the direction of the desired area of the above bone, and the echoes generated from the above bone for each pulse that is emitted are received by each of the ultrasonic transducer elements above, and osteoporosis is diagnosed by predetermined analysis of predetermined received signals after converting the latter into digital echo signals by means of an analogue/digital converter, and which is capable of outputting from the plurality of ultrasonic transducer elements above ultrasonic waves of a waveform represented by Equation (12), towards a predetermined area of the bone above which is the site of measurement.

$$\begin{bmatrix} a_1(t) \\ \vdots \\ a_{N(t)} \end{bmatrix} = F^{-1}\left[T_{(\omega)}^{-1}\begin{bmatrix} 1 \\ \vdots \\ 1 \end{bmatrix}\right] \tag{12}$$

Where $a_1, a_2, \ldots, a_N$ are the incident waves from the 1$^{st}$, 2$^{nd}$, ..., Nth ultrasonic transducer elements, $F^{-1}$ represents a inverse Fourier transformation, $T(\omega)^{-1}$ is an inverse matrix of the matrix $T(\omega)$ in which the elements are Green functions including as variables the distances from any given bone element to any given ultrasonic transducer element.

BRIEF DESCRIPTION OF THE DRAWINGS

FIG. 8 is a view showing the electrical components of an apparatus for diagnosing osteoporosis of a 3$^{rd}$ embodiment of this invention;

BEST MODE FOR CARRYING OUT THE INVENTION

Below, forms of carrying out this invention will be explained, with reference to the diagrams. The explanation will be made more concrete by using practical embodiments.

EMBODIMENT 1

Figure 1:
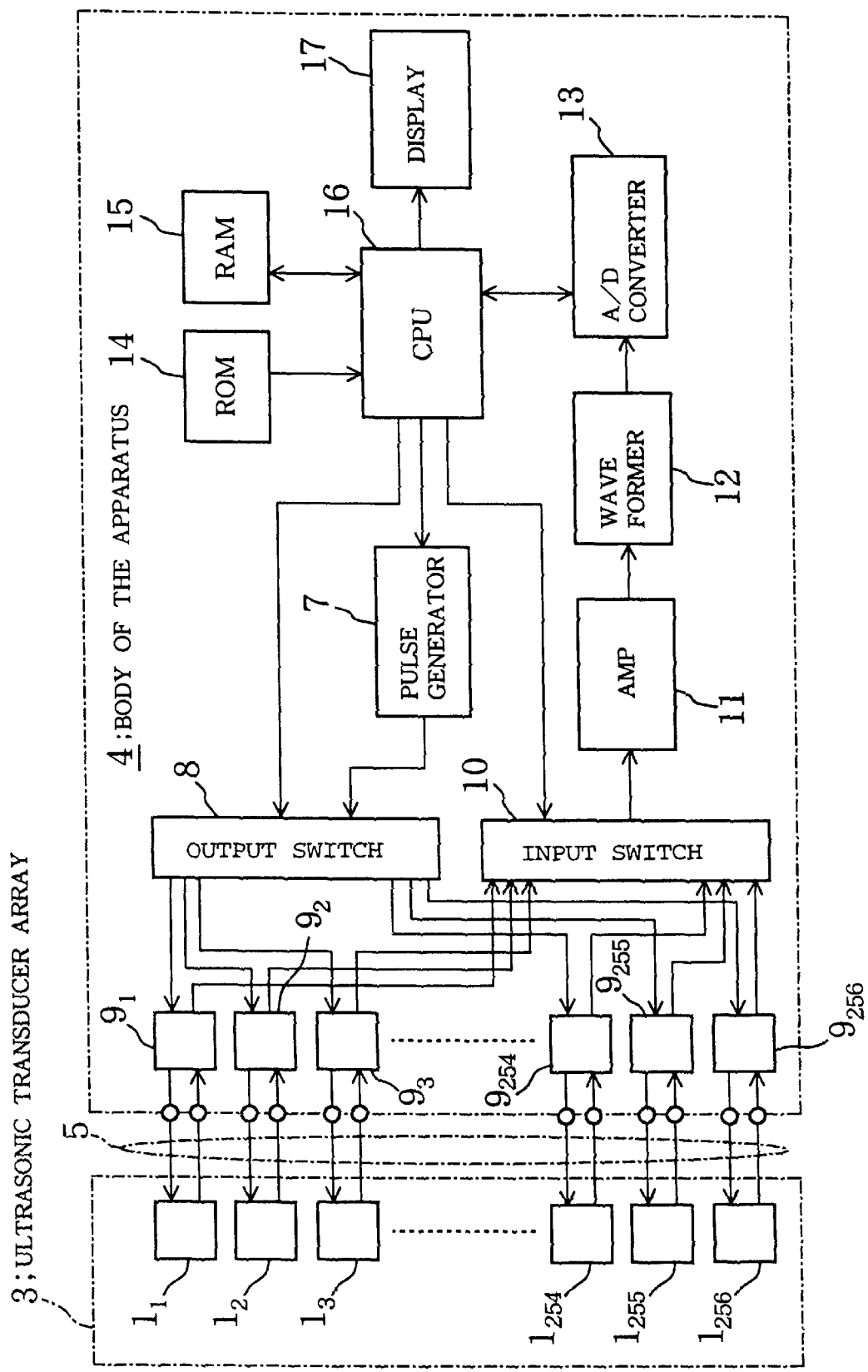
FIG. 1 is a block diagram showing the electrical components of an ultrasonic pulse-echo type apparatus for diagnosing osteoporosis which is a 1$^{st}$ embodiment of the present invention.
Figure 2:
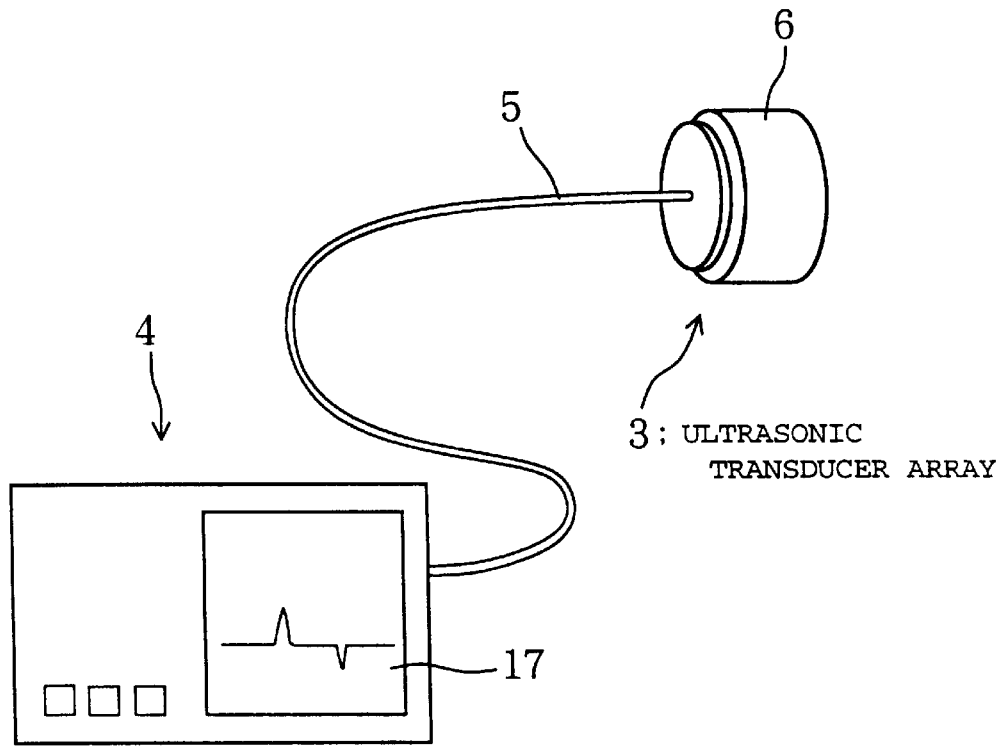
FIG. 2 is an outer view of the same diagnostic apparatus.
Figure 3:
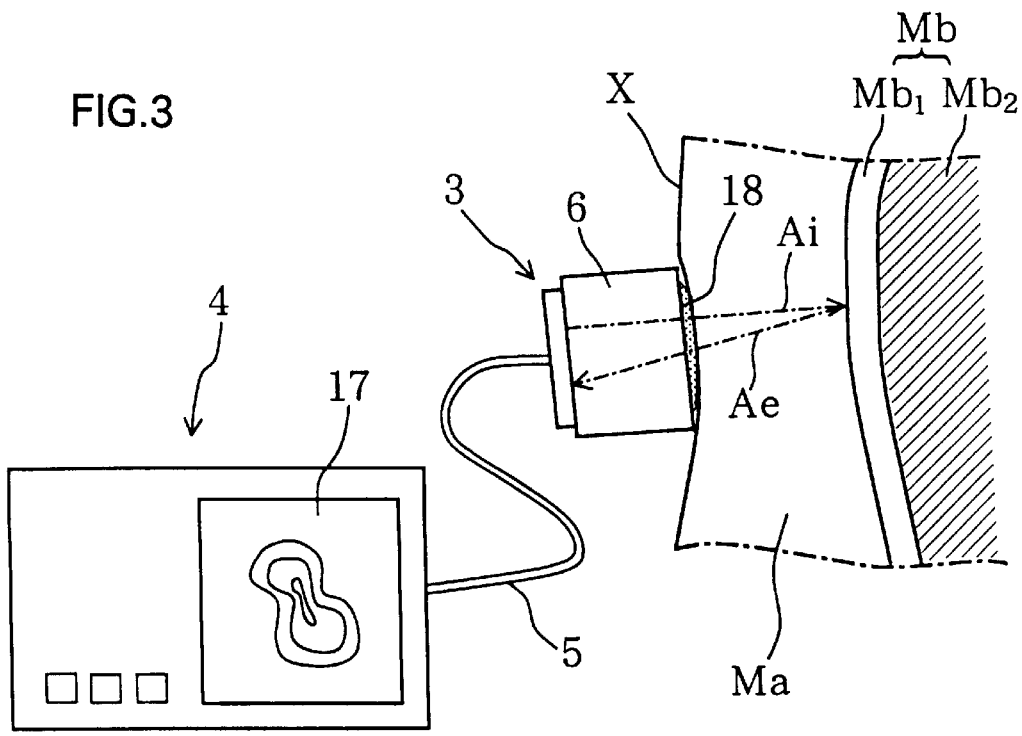
FIG. 3 in a schematic view showing how this diagnostic apparatus is employed.
Figure 4:
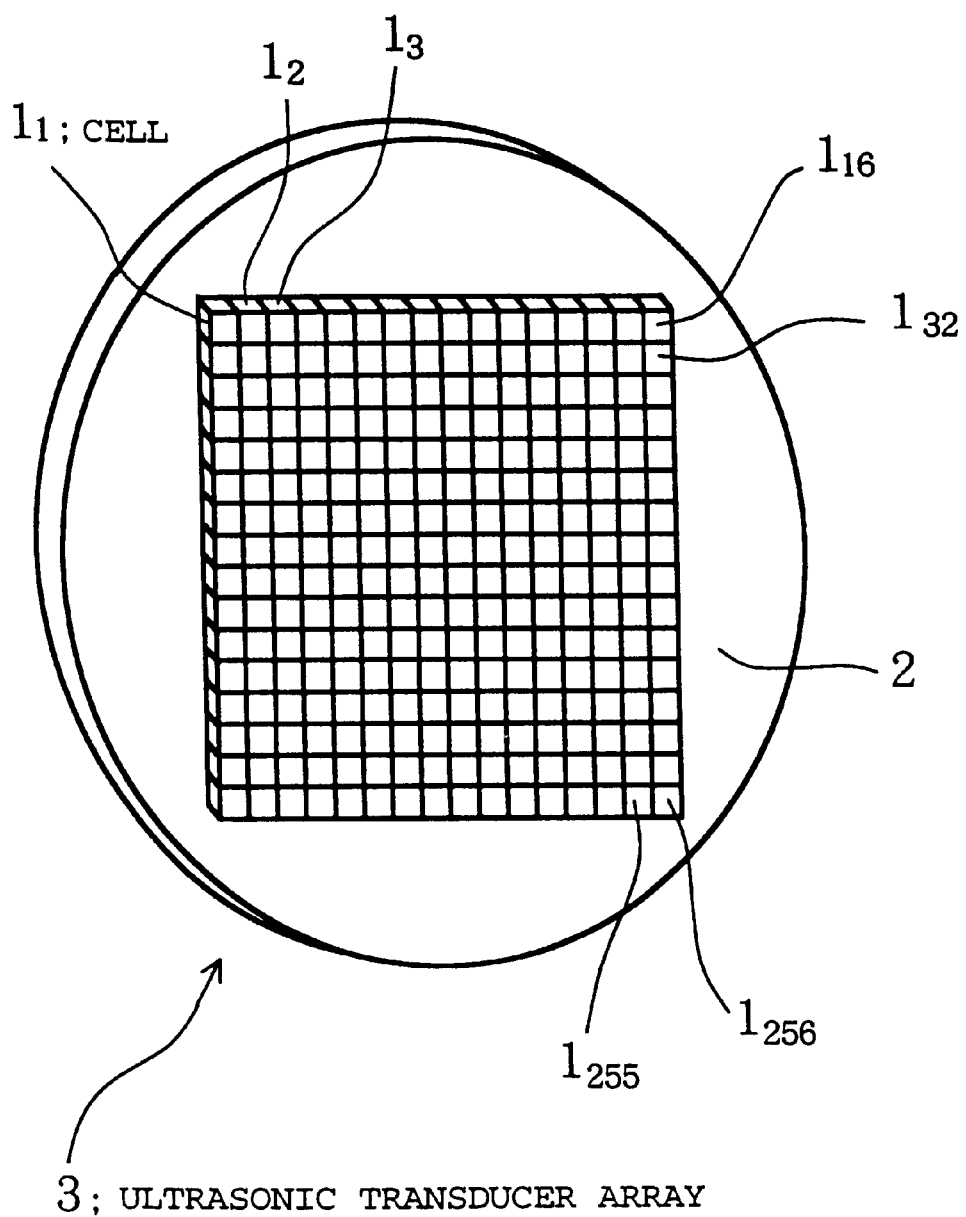
FIG. 4 is an oblique view showing the principal components of the ultrasonic transducer array employed in this diagnostic apparatus.
Figure 5:
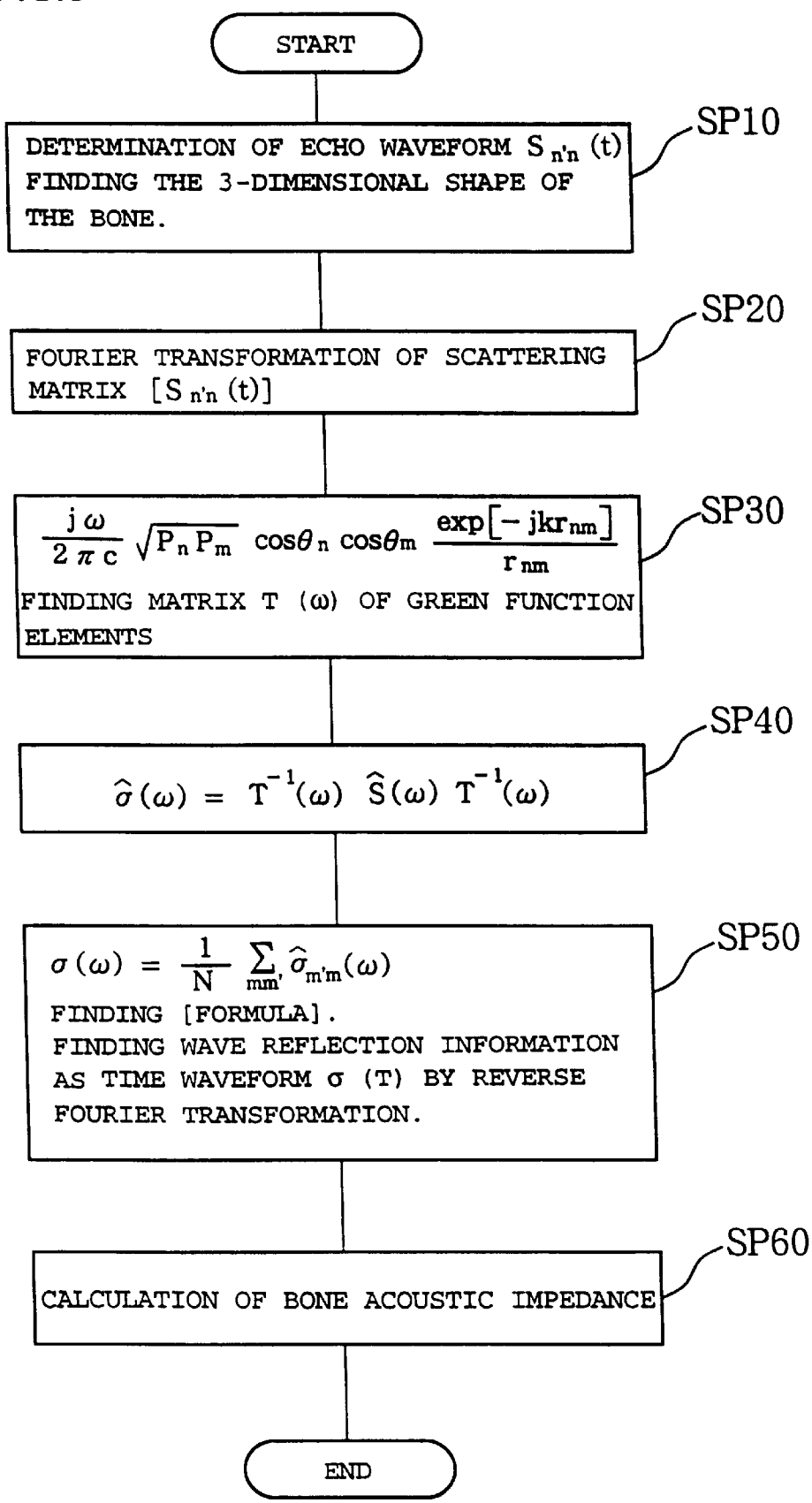
FIG. 5 is a flow chart showing the operating and processing procedure of this diagnostic apparatus.

FIG. 1 is a block diagram showing the electrical components of an ultrasonic pulse-echo type apparatus for diagnosing osteoporosis which is a 1st embodiment of the present invention; FIG. 2 is an outer view of the same diagnostic apparatus; FIG. 3 in a schematic view showing how this diagnostic apparatus is employed; FIG. 4 is an oblique view showing the principal components of the ultrasonic transducer array employed in this diagnostic apparatus; and FIG. 5 is a flow chart showing the operating and processing procedure of this diagnostic apparatus.

To begin with an overall explanation of the components of the device: as FIG. 1 to FIG. 4 show, this embodiment of an apparatus for diagnosing osteoporosis is equipped with an ultrasonic transducer array 3 of a total of 256 transducer cells (termed simply "cells" hereafter) $1_1$, $1_2$, . . . , $1_N$ as ultrasonic transducer elements, arranged 16 across and 16 down on a supporting disk 2; and when the operator begins operation, with this ultrasonic transducer array 3 directed to the bone Mb (cortical bone $Mb_1$, cancellous bone $Mb_2$, see FIG. 3) of the examinee which is the site of measurement, ultrasonic pulses Ai of a frequency in the range 0.54–1.62 MHz (central frequency 1 MHz) are emitted for a number of times discussed below in sequence from the different cells $1_1$, $1_2$, . . . , $1_N$, and the echoes Ae returned from the bone after each pulse are received by the cells $1_1$, $1_2$, . . . , $1_N$; the body of the apparatus 4 takes up the received signals in sequence from each cell $1_1$, $1_2$, . . . , $1_N$ via a cable 5, and osteoporosis is diagnosed by subjecting the received signals to the digital analysis described below.

Each of the parts of the apparatus will next be explained. Each of the cells $1_1$, $1_2$, . . . , $1_N$, is constituted by a thick oscillating piezoelectric element ca. 3 mm square, made of lead zirconate titanate (PZT), etc., having an electrode layer on both sides; one of the electrode surfaces, which becomes the surface which transmits and receives ultrasonic pulse Ai, can have an ordinary ultrasonic retarding spacer 6 of polyethylene in order to eliminate the residual effects of the transmitted signals, if necessary. The ultrasonic retarding spacer 6 may also function as a common support for the cells $1_1$, $1_2$, . . . , $1_N$.

The body of the apparatus 4 is constituted from a pulse generator 7, an output switch 8, matching circuits $9_1$, $9_2$, . . . , $9_N$, an input switch 10, an amplifier 11, a waveform shaper 12, an A/D converter 13, a ROM 14, a RAM 15, a CPU (central processing unit) 16 and a display 17.

The pulse generator 7 produces electrical pulses repeatedly in a predetermined cycle (e.g. 1 msec), and these are transmitted through the output switch, 9, matching circuits $9_1$, $9_2$, . . . , $9_N$ and the cable 5, to the ultrasonic transducer array 3. The output switch 8 is constituted by a number of analogue switches or relays inserted between each of the cells $1_1$, $1_2$, . . . , $1_N$ and the pulse generator 7; and it selects/switches the cells $1_1$, $1_2$, . . . , $1_N$, to which the electrical pulses are fed, in accordance with instruction signals fed from the CPU 16. The matching circuits $9_1$, $9_2$, . . . , $9_N$, are each connected 1-1 with a cell $1_1$, $1_2$, . . . , $1_N$, and match impedance so that the signals can be exchanged between the ultrasonic transducer array 3 and the body of the apparatus 4 without loss of energy.

Similarly, the input switch 10 is constituted by a number of analogue switches or relays inserted between each of the cells $1_1$, $1_2$, . . . , $1_N$, and the amplifier 11; and it selects/switches the cells $1_1$, $1_2$, . . . , $1_N$ from which the received signals are output, in accordance with instruction signals fed from the CPU. The amplifier 11 takes up received signals input through the matching circuits $9_1$, $9_2$, . . . , $9_N$, amplifies them to a predetermined amplitude, and then inputs them to the waveform shaper 12. The waveform shaper 12 comprises an LC bandpath filter; it takes up the received signals amplified by the amplifier 11, shapes the waveforms linearly, and then inputs them to the A/D converter 13.

The A/D converter 13 is provided with a sample hold circuit and a high-speed sampling memory, etc., not shown in the drawings; when the start of sampling is called for by the CPU 16, it samples the signals output from the waveform shaper 12 (waveform shaped analogue received signals) with a predetermined frequency (e.g. 12 MHz), and converts then to digital signals, and after temporarily storing the digitalized echo signals in the high-speed memory, they are sent on to the CPU 16.

The ROM 14 holds the data processing program needed in order to execute the diagnosis of osteoporosis in the CPU 16. This processing program comprises a subprogram for controlling the timing of signal transmission and reception, a subprogram for detecting and processing echo waveforms, a subprogram for calculating the coordinates of bone elements, a subprogram for processing the data to reduce it to a planewave problem, a subprogram for calculating wave reflection information, a subprogram for calculating the acoustic impedance of the bone Mb, and a subprogram for controlling the display of images.

The RAM 15 has a system area for the CPU 16, and a data area for temporary storage of data: echo data, the elements of the scattering matrix, and the coordinates of bone elements, etc., for example, are temporarily stored in the data area.

The CPU 16 executes the above data processing program stored in the ROM 14, using the RAM 15; it controls each of the components of the device such as the pulse generator 7, the output switch 8, the input switch 10 and the A/D converter 13, etc., performs detection and processing of the 256×256 echo waveforms (construction of a scattering matrix), subjects the scattering matrix to Fourier transformation, calculates the coordinates of bone elements, calculates the matrix of Green functions, processes the data to reduce it to a planewave problem (inverse Fourier transformation of the scattering matrix), calculates information on wave reflection, calculates the acoustic impedance of the bone Mb (diagnosis of osteoporosis) and performs 3-dimensional imaging of the shape of the bone Mb.

The calculated impedance of the bone Mb and the 3-dimensional image of the bone Mb are displayed on the display 17 by using a CRT display or liquid crystal display.

The operation of this example (processing flow) will next be explained, with reference to FIG. 5.

Firstly, a bone Mb is selected as the site of measurement which, although not necessarily very flat, has a sufficiently large radius of curvature relative to the wavelength of the ultrasonic pulse Ai.. Good sites of measurement include a lumbar vertebra, humerus, tibia, calcaneus or neck of the femur.

On turning the apparatus on after deciding the site of measurement, the CPU 16 resets all of the components of the apparatus and initializes all counters, resistors and flags, and then waits for the operator to activate the switch for the start of measurements. At this point, the operator smears an ultrasound gel 18 onto the surface of the soft tissue Ma (the skin surface X) covering the bone Mb which is the site of measurement, brings the ultrasonic transducer array 3 into contact with the skin surface X through the ultrasound gel 18, and then turns the switch for the start of measurement to ON. On turning the switch for the start of measurement to ON, the CPU 16 executes each of the processing steps, following the processing procedure shown in FIG. 5.

Firstly, in Step SP10, the CPU 16 finds the 3-dimensional shape of the bone Mb by measuring the waveforms Sn'n (t) of echoes from the bone Mb, under the control of the subprogram for controlling transmission/reception time, the subprogram for echo waveform detection and processing, and the subprogram for calculating the coordinates of bone elements.

Thus, the CPU 16 controls the repeated alternate transmission of ultrasonic pulses Ai and reception of echo signals Ae, 256□□□256 times. When transmitting the ultrasonic pulses Ai, the output switch 8 is controlled so that the electrical pulses are distributed 256 at a time from the $1^{st}$ cell 11 to the $256^{th}$ cell $1_N$. Thus, the $1^{st}$ to $256^{th}$ ultrasonic pulses Ai are emitted from the $1^{st}$ cell 11, and then the $257^{th}$ to $512^{th}$ ultrasonic pulses are emitted from the $2^{nd}$ cell $1_2$, and so on, with the (256n−255)th to 256nth ultrasonic pulse being emitted from the nth cell.

When receiving the echo signals Ae, on the other hand, the input control switch is controlled so that for each signal received each time the cells $1_1, 1_2, \ldots, 1^N$ are switched in sequence so as to extract the received signals. As a result, in the case of the $1^{st}$ echo Ae, only the signal reception signal output from the 1th cell $1_1$ is introduced to the A/D converter 13, in the case of the $2^{nd}$ echo Ae, only the signal reception signal output from the $2^{nd}$ cell $1_2$ is introduced to the A/D converter 13, and in the case of the nth echo Ae only the signal reception signal output from the nth cell $1_n$ is introduced to the A/D converter 13. By doing this, echo waveforms $S_{n'n}$ (t) as a function of time t, when an ultrasonic pulse Ai is emitted from the nth cell $1_n$ and the signal of the echo Ae from the bone Mb at this time is received by the n'th cell $1_{n'}$, are measured for all of the 256×256 combinations.

Figure 6:
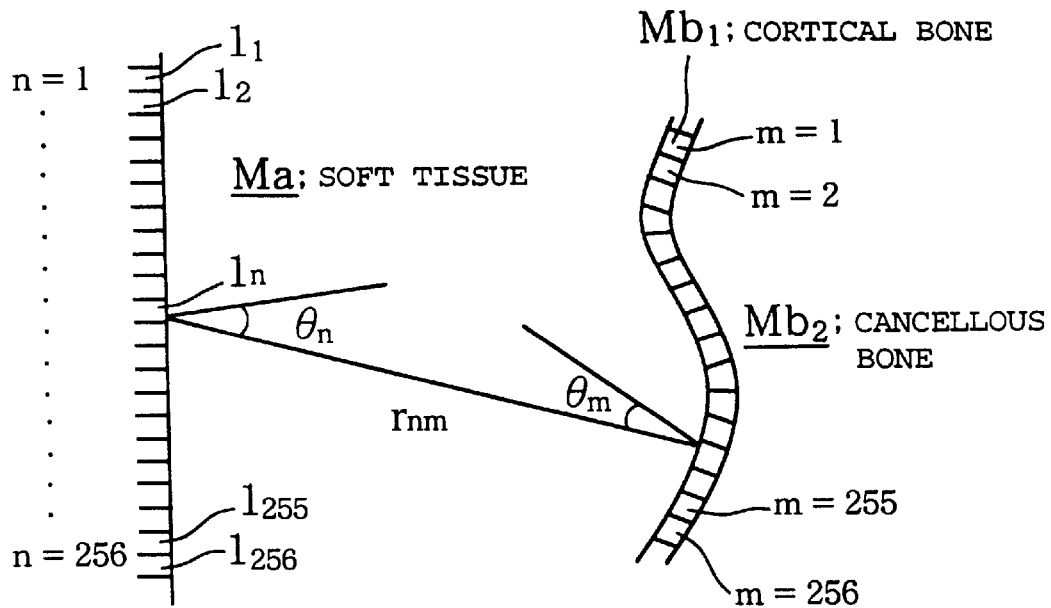
FIG. 6 is an explanatory view of the operation of this embodiment.

The measured echo waveforms $S_{n'n}$ (t) from the bone Mb are used as the basis for finding the 3-dimensional shape of the bone Mb, by means of a data processing algorithm resembling the C-mode ultrasonic echo method. As a result, the surface shape of the bone Mb, comprising 256 bone elements, the same number as the number of cells $1_1, 1_2, \ldots, 1_N$ (see FIG. 6), is found in the form of a collection of 3-dimensional coordinates for each of the bone elements. This is used to enable the CPU 16 to display a 3-dimensional image of the shape of the bone Mb on the display screen 17 (see FIG. 3).

The CPU 16 then moves on to Step SP20, and subjects the 256×256 scattering matrix $[S_{n'n}(t)]$, which displays the 256×256 echo waveforms $S_{n'n}$ (t) measured in Step SP10 in the form of a matrix, to Fourier transformation with time t (see Equation (13)), under the control of the planewave problem attribution subprogram.

$$S(t) = [S_{n'n}(t)] \xrightarrow{\text{Fourier transform}} \hat{S}(\omega) \tag{13}$$

The CPU 16 then goes onto processing in Step SP20 to SP40, under the control of the planewave problem attribution subprogram.

In Step SP30, the CPU 16 calculates the distances from the mth bone element to the nth cell $_{mn}$ (see FIG. 6), from the bone element coordinates calculated in Step SP10; it finds a 256×256 matrix T(ω) in which the elements are Green functions given by Equation (14), and then in Step SP40 calculates a 256×256 scattering matrix σ (ω) given by Equation (15). In passing σ (ω) is the scattering matrix for the bone Mb at the interface of the cortical bone $Mb_1$ and the cancellous bone $Mb_2$, whereas $[S_{n'n}$ (t)] is the scattering matrix for the bone Mb, taking into account the delay in propagation of the echoes Ae returned in the soft tissue Ma, and is calculated as above.

$$\frac{j\omega}{2\pi c}\sqrt{P_n P'_m}\cos\theta_n\cos\theta_m\frac{\exp[-jkr_{nm}]}{r_{nm}} \tag{14}$$

Here, $P_n$ is the surface area of the nth cell, and $P_m$ is the surface area of the mth cell.

$$\hat{\sigma}(\omega)=T^{-1}(\omega)\hat{S}(\omega)T^{-1}(\omega) \tag{15}$$

$\hat{\sigma}(\omega)$: scattering matrix of bone
Here, $T(\omega)^{-1}$ is the inverse matrix of the matrix T (ω) in which the elements are Green functions (Equation (14)). Equation (15) which gives the scattering matrix of the bone a (ω) is derived as follows.

Any given combination of pulses Ai emitted from a cell $1_1, 1_2, \ldots, 1_N$ and positions on the cortical bone $Mb_1$ can be represented as in Equation (16).

$$\begin{matrix}\text{Wave incident} & \text{output from the} \\ \text{to the bone} & \text{transducer array}\end{matrix} \tag{16}$$

$$\begin{bmatrix}b_1\\b_2\\\vdots\\b_N\end{bmatrix} = \hat{T}(\omega)\begin{bmatrix}a_1\\a_2\\\vdots\\a_N\end{bmatrix}$$

Here, $a_1, a_2, \ldots, a_N$, are waves emitted from each of the cells $1_1, 1_2, \ldots, {}^1N$, and $b_1, b_2, \ldots, b_N$, are waves incident to the different elements of cortical bone $Mb_1$ (m=1, 2, …, N×N=256).

The ultrasonic pulses Ai incident to the cortical bone $Mb_1$ are then scattered inside the bone (and more particularly at the interface between the cortical bone $Mb_1$ and the cancellous one $Mb_2$) and the amplitudes of the scattered waves $C_1, C_2, \ldots, C_N$ at the surface of each of the bone elements (m=1, 2, …, N×N=256) when they are re-emitted to the soft tissue are given by Equation (17).

$$\text{Scattered waves from bone} \tag{17}$$

$$\begin{bmatrix}c_1\\c_2\\\vdots\\c_N\end{bmatrix} = \hat{\sigma}(\omega)\begin{bmatrix}b_1\\b_2\\\vdots\\b_N\end{bmatrix}$$

$\hat{\sigma}(\omega)$: scattering matrix of the bone

The waveforms of the echoes Ae when the scattered waves from the bone Mb are returned to the cells $1_1, 1_2, \ldots, 1_N$ (received waveforms) are given by Equation (18).

$$\text{Waveform of the signal received at the transducer array} \tag{18}$$

$$\begin{bmatrix}d_1\\d_2\\\vdots\\d_N\end{bmatrix} = \hat{T}(\omega)\begin{bmatrix}c_1\\c_2\\\vdots\\c_N\end{bmatrix}$$

Here, $d_1, d_2, \ldots, d_N$ represent the amplitudes of the signals received at each of the cells $1_1, 1_2, \ldots, 1_3$.

Therefore, linking Equation (16), Equation (17) and Equation (18) gives Equation (19); and Equation (15) which gives the scattering matrix of bone σ(ω) is obtained from Equation (19).

$$\hat{S}(\omega) = \hat{T}(\omega)\hat{\sigma}(\omega)\hat{T}(\omega) \tag{19}$$

Figure 7:
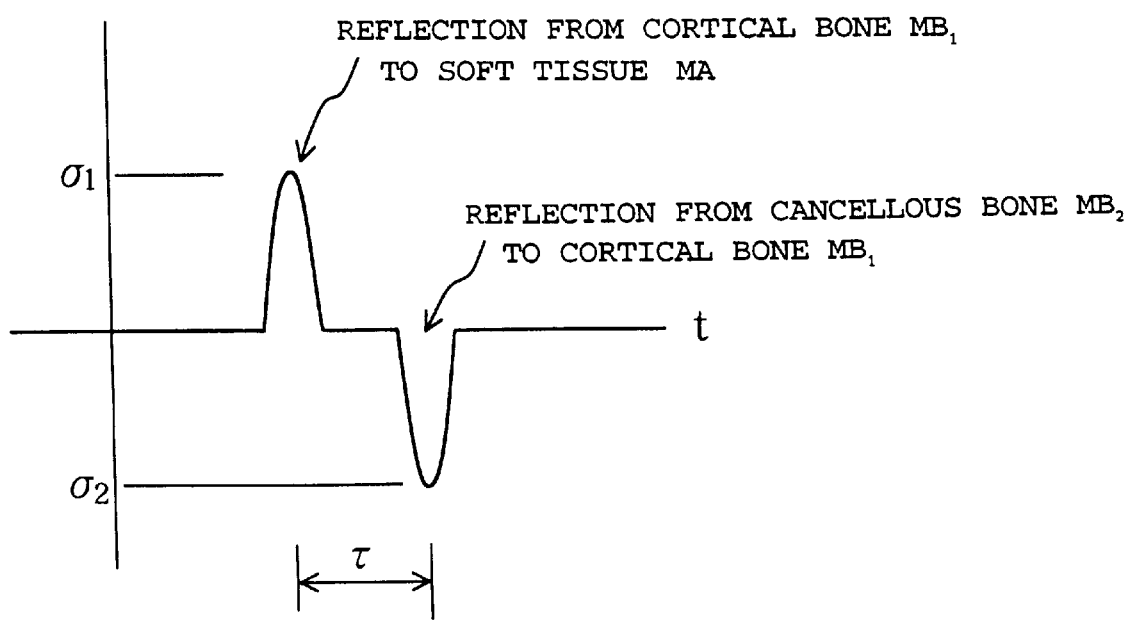
FIG. 7 is an explanatory view of the operation of this embodiment.

In Step SP50, under the control of the planewave problem attribution subprogram and the subprogram for calculating wave reflection information, the CPU 16 then finds Equation (20), subjects this to inverse Fourier transformation, and finds the time waveform of the wave reflection information σ(t). By doing this, as FIG. 7 shows, information on wave reflection (reflection coefficient) $\sigma_1$ from the cortical bone $Mb_1$ to the soft tissue Ma, and information on wave reflection $\sigma_2$ from cancellous bone $Mb_2$ to cortical bone $Mb_1$ can be found.

$$\sigma(\omega) = \frac{1}{N}[1\,1\,\ldots\,1]\hat{\sigma}(\omega)\begin{bmatrix}1\\1\\1\\\vdots\end{bmatrix} \tag{20}$$

$$= \frac{1}{N}\sum_{mm'}\hat{\sigma}(\omega)_{m'm}$$

Equation (20) is derived as follows.

The amplitudes of waves scattered from the bone Mb when the wavefront of the ultrasonic waves Ai incident to the cortical bone $Mb_1$ is parallel to the surface of the cortical bone are given by Equation (21), derived from Equation (16) and Equation (17).

$$\begin{bmatrix}c_1\\c_2\\\vdots\\c_N\end{bmatrix} = \hat{\sigma}(\omega)\begin{bmatrix}1\\1\\1\\\vdots\end{bmatrix} \tag{21}$$

Thus, in Equation (21), provided that the thickness of the cortical bone $Mb_1$ is uniform and that the radius of curvature of the cortical bone $Mb_1$ is sufficiently large compared with the wavelength of the incident ultrasonic waves, Equations (22) holds and hence, taking the average to be σ (ω), Equation (20) holds.

$$C_1 = C_2 = C_N \tag{22}$$

σ (ω) here is the sum of the elements σ $(\omega)_{m'm}$ of a square matrix (in this example a 256×256 square matrix), and the physical meaning of elements σ $(\omega)_{m'm}$ is the ratio of the incident sound wave when the ultrasonic pulse Ai is incident from the soft tissue Ma on the mth bone element, and the sound wave re-emitted to the soft tissue Ma from the m'th bone element after scattering of the sound wave inside the bone.

Next, the physical meaning of σ (ω), in other words the physical meaning of the sum of the elements σ $(\omega)_{m'm}$ of the square matrix, is as follows.

In Equation (20) the elements of the vertical matrix on the right hand side are all "1", and hence the ultrasonic waves Ai incident to each of the bone elements have the same amplitude and phase; however, this acoustically equivalent to plane wavefronts incident on the surface of the bone Mb. And provided that the thickness of the cortical bone $Mb_1$ is uniform, wavefronts parallel to the surface of the bone Mb are reflected in the same way at the interface between the cortical bone $Mb_1$ and the cancellous bone $Mb_2$, are propagated inside the cortical bone $Mb_1$ maintaining the wavefront parallel to the surface of the cortical bone $Mb_1$, and emitted to the soft tissue with a parallel wavefront. This means that the waves in each element are equalized, and are uniform in amplitude and phase. Therefore, because the reflecting surface and the wavefront are parallel, this problem reduces to a simple planewave problem.

After this, the CPU 16 proceeds to Step SP60, and finds the acoustic impedance $Zb_1$ of the cortical bone $Mb_1$ and the acoustic impedance $Zb_2$ of the cancellous bone $Mb_2$ on the basis of Equation (23) and Equation (24), under the control of the subprogram for calculating the impedance of the bone Mb.

$$Zb_1 = \frac{1+\sigma_1}{1-\sigma_1}Za \tag{23}$$

Za : already known

Where Za represents the acoustic impedance of the soft tissue Ma.

$$Zb_2 = \frac{1+\frac{\sigma_2}{1-\sigma_1^2}}{1-\frac{\sigma_2}{1-\sigma_1^2}}Zb_1 \tag{24}$$

Equation (23) and Equation (24) are given from Equation (25) and Equation (26).

$$\sigma_1 = \frac{-Za+Zb_1}{Za+Zb_1} \tag{25}$$

$$\sigma_2 = \frac{-Zb_1+Zb_2}{Zb_1+Zb_2}\sqrt{1-\sigma_1^2}\sqrt{1-\sigma_1^2} \tag{26}$$

In passing, as FIG. 7 shows, the surface density ($\tau.Zb_1$) of the cortical bone $Mb_1$ can be found from the difference τ in the timing of the reception of the signal for the wave reflected from the interface of the soft tissue Ma and the cortical bone $Mb_1$, and the timing for the reception of the signal for the wave reflected from the interface of the cortical bone $Mb_1$ and the cancellous bone $Mb_2$.

With the constitution of this example, progress in osteoporosis is diagnosed from the calculated acoustic impedance of the bone Mb.

The acoustic impedance of the bone is given by the square root of "bone elasticity□□□bone density", and the two parameters "bone elasticity" and "bone density" are related in such a way that as one increases (or decreases), the other also increases (or decreases). Therefore, as bone density increases (or decreases), elasticity also increases (or decreases), and impedance responds sensitively with an increase (or decrease) as the multiplicative effect of the two factors. Therefore, acoustic impedance is a very good indicator for judging bone density. For example, when the acoustic impedance of the bone of an examinee is much smaller than the average value for the age group, it can be judged that there has been a deterioration in osteoporosis in the bone.

Also with the constitution of this example, bones which are not very flat can be used as the site of measurement, and the direction of the ultrasonic transducers is not a problem because data on wave reflection from the bone are processed to enable it to be handled as a planewave problem. In other words, the acoustic impedance of the bone can be determined irrespective of its smoothness and shape, which makes the method very convenient and reliable. The fact that it is also possible to find the acoustic impedances of both cortical bone and interfacial bone greatly raises reliability. Displaying a 3-dimensional image of the bone using the display 17 also greatly increases the amount of diagnostic information.

EMBODIMENT 2

A $2^{nd}$ embodiment of this invention will next be explained.

This $2^{nd}$ embodiment has the same constitution as Embodiment 1, except that the method for processing data on waves reflection from the bone of the measurement site so as to reduce it to a planewave problem differs from that of Embodiment 1.

Thus, in this $2^{nd}$ embodiment, ultrasonic waves of a waveform represented by Equation (27) are output almost simultaneously from the plurality of cells $1_1, 1_2, \ldots, 1_N$, towards the measurement site on the bone Mb. The output wavefront is $$\begin{bmatrix} a_{1(t)} \\ \vdots \\ a_{N(t)} \end{bmatrix} = F^{-1}\left[T_{(\omega)}^{-1}\begin{bmatrix} 1 \\ \vdots \\ 1 \end{bmatrix}\right] \tag{27}$$

Where $a_1, a_{21}, \ldots, a_N$ are the waves emitted from each of the cells $1_1, 1_2, \ldots, 1_N$, $F^{-1}$ represents an inverse Fourier transformation, $T(\omega)^{-1}$ is the inverse matrix of the matrix $T(\omega)$ in which the elements are the Green functions including as variables the distances from any given bone element to any given cell.

This time, the echoes Ae received at each of the cells $1_1, 1_2, \ldots, 1_N$ (Equation (28)) are subjected to Fourier transformation to find Equation (29); then Equation (30) is found (this Equation (30) corresponds to Equation (20) in Embodiment 1). Equation (30) is then subjected to inverse Fourier transformation in order to find the time waveform of the wave reflection information $\sigma$ (t). In this way it is possible to find information on wave reflection (reflection coefficient) $\sigma_1$ from the cortical bone $Mb_1$ to the soft tissue Ma, and information on wave reflection (coefficient of reflection) $\sigma_2$ from the cancellous bone $Mb_2$ to the cortical bone $Mb_1$ (FIG. 7).

$$\begin{bmatrix} e_{1(t)} \\ \vdots \\ e_{N(t)} \end{bmatrix} \tag{28}$$

Where $e_1, e_2, \ldots, e_N$ represent the signals received at each of cells $1_1, 1_2, \ldots, 1_N$.

$$\begin{bmatrix} \hat{e}_{1(\omega)} \\ \hat{e}_{N(\omega)} \end{bmatrix} \tag{29}$$

$$\sigma(\omega) = \frac{[1\,1\ldots 1]}{N} T_{(\omega)}^{-1} \begin{bmatrix} \hat{e}_{1(\omega)} \\ \hat{e}_{N(\omega)} \end{bmatrix} \tag{30}$$

Thus, this $2^{nd}$ embodiment can give similar benefits to those of Embodiment 1.

EMBODIMENT 3

Figure 8:
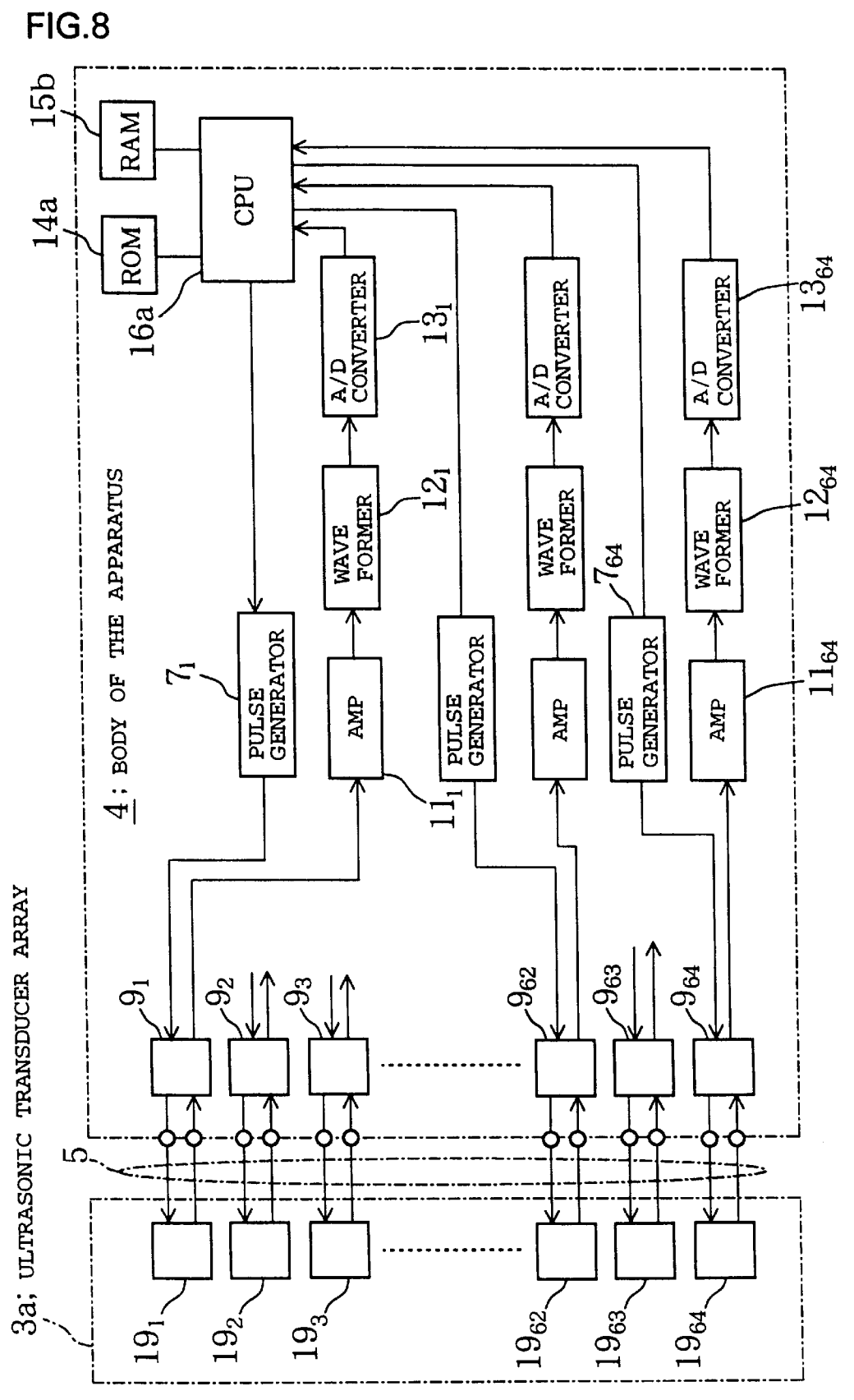

FIG. 8 is a block diagram showing the electrical components of an apparatus for diagnosing osteoporosis which is a $3^{rd}$ embodiment of this invention.

As FIG. 8 shows, the major difference in the constitution of this $3^{rd}$ embodiment compared with that of Embodiment 1 above is that in the body of the apparatus 4 there are dedicated pulse generators $7_1, 7_2, \ldots, 7_{64}$, amplifiers $11_1, 11_2, \ldots, 11_{64}$, waveformers $12_1, 12_2, \ldots, 12_{64}$ and A/D converters $13_1, 13_2, \ldots, 13_{64}$ for each of the cells $19_1, 19_2, \ldots, 19_{64}$, making the output switch 8 and the input switch 10 uN×Necessary. The ultrasonic transducer array 3a in this embodiment is constituted by an arrangement of 64 square cells $19_1, 19_2, \ldots, 19_{64}$ of approximately 1 mm×1 mm, 8 across and 8 down at a pitch of 4 mm.

With the constitution of this $2^{nd}$ [sic] embodiment, on transmitting an ultrasonic pulse Ai of a frequency in the range 0.54–1.62 MHz (central frequency 1 MHz) from the kth cell $19_k$, echoes Ae are received by all of the cells $19_1, 19_2, \ldots, 19_{64}$; and these are input to the respective amplifiers $11_1, 11_2, \ldots, 11_{64}$, waveformers $12_1, 12_2, \ldots, 12_{64}$ and A/D converters $13_1, 13_2, \ldots, 13_{64}$, and taken up by the CPU 16a.

Consequently, whereas in Embodiment 1 ultrasonic pulses Ai need to be transmitted N×N times (where N is the number of cells), in this embodiment N times is sufficient. Therefore, with the constitution of this embodiment processing is N times faster.

EMBODIMENT 4

The major difference in the constitution of this $4^{th}$ embodiment compared with the constitutions of Embodiments 1–3 is that the coefficient of reflection $\lambda$a at the interface between the soft tissue Ma and the bone Mb can be determined without previously determining the shape of the bone. The components of the hardware of the apparatus are the same as in FIG. 8 (Embodiment 2 [sic]).

In this embodiment the coefficient of reflection $\lambda$a at the interface between the soft tissue Ma and the bone Mb is handled by finding eigenvalues of an N×N real symmetrical matrix (Equation (31)).

$$\begin{bmatrix} Re(S(\omega)) & -Im(S(\omega)) \\ -Im(S(\omega)) & -Re(S(\omega)) \end{bmatrix} \tag{31}$$

The way in which the coefficient of reflection $\lambda$a at the interface between the soft tissue Ma and the bone Mb is handled by finding eigenvalues of an N×N real symmetrical matrix (Equation (31)) is explained below.

Figure 9:
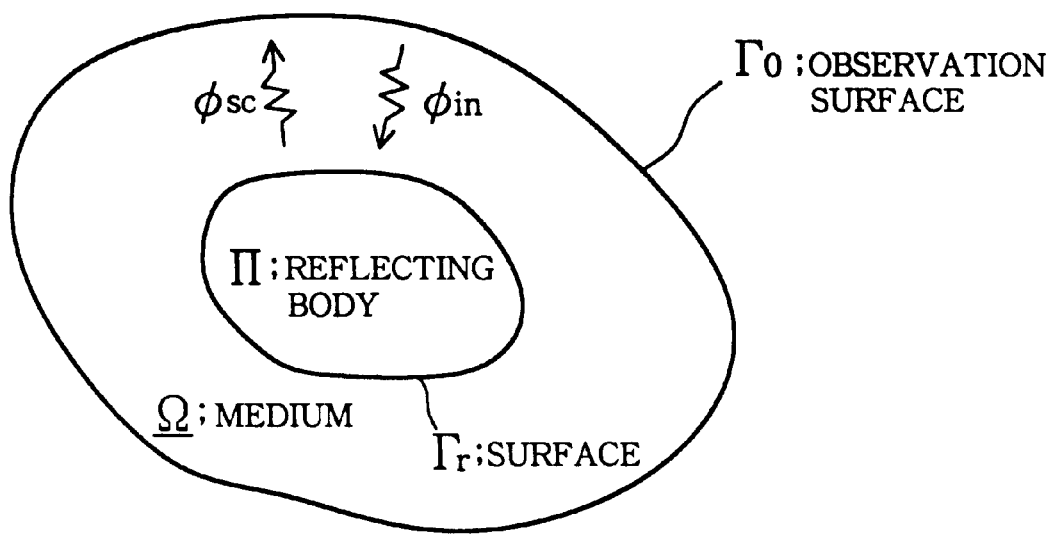
FIG. 9 is a view explaining the set-up process in a 4$^{th}$ embodiment of the present invention.

As FIG. 9 shows, there is an observation surface $\Gamma_0$ on the closed curved surface surrounding the reflecting body $\pi$. A large transducer array is placed on this observation surface $\Gamma_0$, so as to be able to transmit given waves $\phi_{in}$ towards the reflecting body $\pi$. At t<0, a wave $\phi_{in}$ is transmitted from the observation surface $\Gamma_0$, and at t=−0 a wavefront is formed along the surface $\Gamma_r$ of the reflecting body. Assuming that the coefficient of perpendicular reflection of the reflecting body $\pi$ is a constant (real number) which does not depend on the frequency $\omega$, and moreover that the wave is not attenuated in the medium $\Omega$ between the reflecting body $\pi$ and the observation surface $\Gamma_0$, the relationship shown in Equation (32) holds within the medium $\Omega$.

$$\phi_{sc}(x,t) = \lambda \phi_{in}(x,-t), (t>0) \tag{32}$$

Here, $\phi_{in}$ is the wave function of the wave incident to the reflecting body $\pi$, $\phi_{sc}$ is the wave function of the scattered wave returned from the reflecting body $\pi$, and $^x$ is the coordinate of the site.

Multiplying both sides of Equation (32) by exp (-jωt), and integrating with respect to time gives $$\text{Left side} \equiv \int_{-\infty}^{\infty} \phi_{sc}(x,t)e^{-j\omega t}dt = \hat{\phi}_{\omega sc}(x) \tag{33}$$

$$\text{Right side} \equiv \int_{-\infty}^{\infty} \lambda\phi_{in}(x,-t)e^{-j\omega t}dt \tag{34}$$

$$= \lambda \int_{-\infty}^{\infty} \phi_{in}(x,t)e^{+j\omega t}dt = \lambda \hat{\phi}_{\omega in}^*(x)$$

and from Equation (33) and Equation (34), Equation (35) is obtained $$\hat{\phi}_{sc}(\omega,x) = \lambda\hat{\phi}^*_{in}(\omega,x) \tag{35}$$

In general, the relationship between an incident wave and a scattered waves is shown by Equation (36).

$$\left(\left(\hat{\phi}_{sc}(\omega, x)\right)\right)_{x \in \Gamma_0} = \int_{\Gamma_0} \sigma(\omega, x, x') \hat{\phi}_{in}(\omega, x') dx' \tag{36}$$

Where $\sigma(\omega, x, x')$ is the scattering parameter when a wave output from a wave source on $x'$ is scattered by the surface $\Gamma_r$ of the reflecting body $\pi$ and formed on $x$.

Equation (37) can be derived from Equation (35) and Equation (36).

$$S_{r0}\sigma(\omega, x, x')\hat{\phi}_{in}(\omega, x')dx' = \lambda\hat{\phi}^*_{in}(\omega, x) \tag{37}$$

In order to processes the se parate elements of Equation (37), the observation surface $F_0$ is divided into a small grid $\Delta j=0, 1, \ldots, N-1$. The grid $\Delta j=0, 1, \ldots, N-1$ here corresponds to the width (surface area) of the small cells. Since changes in $\phi_{in}$ and $\phi_{sc}$ within the grid can be ignored, Equation (37) can be represented in the form of Equation (38).

$$\sum_j \sigma(\omega, x_i, x_j)\hat{\phi}_{in}(\omega, x_j)\Delta_j = \lambda\hat{\phi}^*_{in}(\omega, x_i) \tag{38}$$

Modifying both sides of Equation (38) by multiplying $\Delta^{1/2}$ gives Equation (39).

$$\sum_j \sigma(\omega, x_i, x_j)\sqrt{\Delta_i}\sqrt{\Delta_j}\left(\hat{\phi}_{in}(\omega, x_j)\sqrt{\Delta_j}\right) = \lambda\left(\hat{\phi}^*_{in}(\omega, x_i)\sqrt{\Delta_i}\right) \tag{39}$$

Replacing the contents of the brackets ( ) with $\Psi_{in}(\omega, j)$, and making $\sigma(\omega, x_I, x_j)\Delta I^{1/2}\Delta j^{1/2} = S(\omega, I, j)$, gives Equation (40). $S(\omega, I, j)$ is the separated scattering parameter, when a signal (transmitted wave) output from the jth grid element (cell) is scattered by the surface $\Gamma_r$ of the reflecting body $\pi$ and returned as an input signal (received signal) to the ith grid element (cell).

$$\Psi_{SC}(\omega, i) = \sum_j S(\omega, i,j)\Psi_{in}(\omega, j) = \lambda\Psi^*_{in}(\omega, i) \tag{40}$$

Where $\Psi_{sc}(\omega, I)$ means the input signal (received signal) when the unit output signals output from all of the N grid elements (cells) are scattered by the reflecting body and returned to the ith grid element (cell).

Writing Equation (40) in the form of a matrix equation, it can be represented by Equation (41), Equation (42) and Equation (43).

$$S_\omega = \begin{bmatrix} S_{(\omega,0,0)} & S_{(\omega,0,1)} & \cdots & S_{(\omega,0,N-1)} \\ S_{(\omega,1,0)} & & & S_{(\omega,1,N-1)} \\ \vdots & & & \vdots \\ S_{(\omega,N-1,0)} & \cdots & \cdots & S_{(\omega,N-1,N-1)} \end{bmatrix} \tag{41}$$

$$\vec{\Psi}_{in(\omega)} = \begin{bmatrix} \Psi_{in(\omega,0)} \\ \Psi_{in(\omega,1)} \\ \vdots \\ \Psi_{in(\omega,N-1)} \end{bmatrix} \tag{42}$$

$$S_{(\omega)}\vec{\Psi}_{in(\omega)} = \lambda\vec{\Psi}^*_{in(\omega)} \tag{43}$$

This scattering parameter $S(\omega)$ is an N×N complex symmetrical matrix, and can be obtained by measurement. Separating the real and imaginary parts of Equation (43) gives Equation (44) and Equation (45).

$$Re(S(\omega))Re(\Psi_{in}(\omega)) - Im(S(\omega))Im(\Psi_{in}(\omega))$$

$$= \lambda Re(\Psi_{in}(\omega)) \tag{44}$$

$$Im(S(\omega))Re(\Psi_{in}(\omega)) + Re(S(\omega))Im(\Psi_{in}(\omega))$$

$$= -\lambda Im(\Psi_{in}(\omega)) \tag{45}$$

By multiplying both sides of Equation (45) by −1 and writing Equation (44) and Equation (45) in matrix form, Equation (46) is obtained.

$$\begin{bmatrix} Re(S(\omega)) & -Im(S(\omega)) \\ -Im(S(\omega)) & -Re(S(\omega)) \end{bmatrix} \begin{bmatrix} Re(\vec{\Psi}_{in}(\omega)) \\ Im(\vec{\Psi}_{in}(\omega)) \end{bmatrix} = \lambda \begin{bmatrix} Re(\vec{\Psi}_{in}(\omega)) \\ Im(\vec{\Psi}_{in}(\omega)) \end{bmatrix} \tag{46}$$

Because the scattering parameter $S(\omega)$ here is an N×N symmetrical matrix, the form of Equation (46) indicates that the coefficient of perpendicular reflection $\lambda$ of the reflecting body $\pi$ is a 2N×2N symmetrical matrix eigenvalue problem. Therefore $\lambda$ is ordinarily a real number.

When the eigenvector of Equation (34) with respect to $\lambda$ is $$\begin{bmatrix} Re\vec{\Psi}_{in}(\omega) \\ Im\vec{\Psi}_{in}(\omega) \end{bmatrix}$$

multiplying $$\begin{bmatrix} Re(S(\omega)) & -Im(S(\omega)) \\ -Im(S(\omega)) & -Re(S(\omega)) \end{bmatrix}$$

by $$\begin{bmatrix} Im(\vec{\Psi}_{in}(\omega)) \\ -Re(\vec{\Psi}_{in}(\omega)) \end{bmatrix}$$

from the left hand side gives $$\begin{bmatrix} Re(S(\omega)) - Im(S(\omega)) \\ -Im(S(\omega)) - Re(S(\omega)) \end{bmatrix} \begin{bmatrix} Im(\vec{\Psi}_{in}(\omega)) \\ -Re(\vec{\Psi}_{in}(\omega)) \end{bmatrix} = \tag{48}$$

$$\begin{bmatrix} Re(S(\omega))Im(\vec{\Psi}_{in}(\omega)) + Im(S(\omega))Re(\vec{\Psi}_{in}(\omega)) \\ -Im(S(\omega))Im(\vec{\Psi}_{in}(\omega)) + Re(S(\omega))Re(\vec{\Psi}_{in}(\omega)) \end{bmatrix} =$$

$$\begin{bmatrix} -\lambda Im(\vec{\Psi}_{in}(\omega)) \\ -\lambda \times -Re(\vec{\Psi}_{in}(\omega)) \end{bmatrix} = -\lambda \begin{bmatrix} Im\vec{\Psi}_{in}(\omega) \\ -Re\vec{\Psi}_{in}(\omega) \end{bmatrix}$$

$$\therefore \lambda \begin{bmatrix} Re\,\Psi_{in} \\ Im\,\Psi_{in} \end{bmatrix} = \begin{bmatrix} ReS & -ImS \\ -ImS & -ReS \end{bmatrix} \begin{bmatrix} Re\,\Psi_{in} \\ Im\,\Psi_{in} \end{bmatrix} \tag{49}$$

therefore $-\lambda$ is the eigenvalue of $$\begin{bmatrix} ReS(\omega) & -ImS(\omega) \\ -ImS(\omega) & -ReS(\omega) \end{bmatrix}$$

The eigenvector is $$\begin{bmatrix} Im(\vec{\Psi}_{in}(\omega)) \\ -Re(\vec{\Psi}_{in}(\omega)) \end{bmatrix}$$

and this corresponds to $I\Psi_{in}(\omega)$.

Consequently $\lambda$, the eigenvalue of Equation (46), exists as N positive eigenvalues $\lambda_0, \lambda_1, \ldots, \lambda_{N-1}$, and N×Negative eigenvalues $-\lambda_0, -\lambda_1, \ldots, \lambda_{N-1}$. The largest eigenvalue (absolute value) $\lambda_0$ corresponds to the greatest coefficient of reflection. However, in practice, because of the frequency characteristics of the cells, $\lambda_0$ is proportional to the coefficient of reflection of the object. Accordingly, in this embodiment, the proportionality constant is obtained by determining the scattering parameter of an object of known coefficient of reflection λb, and calculating the largest eigenvalue (absolute value) $\lambda_0$.

Figure 10:
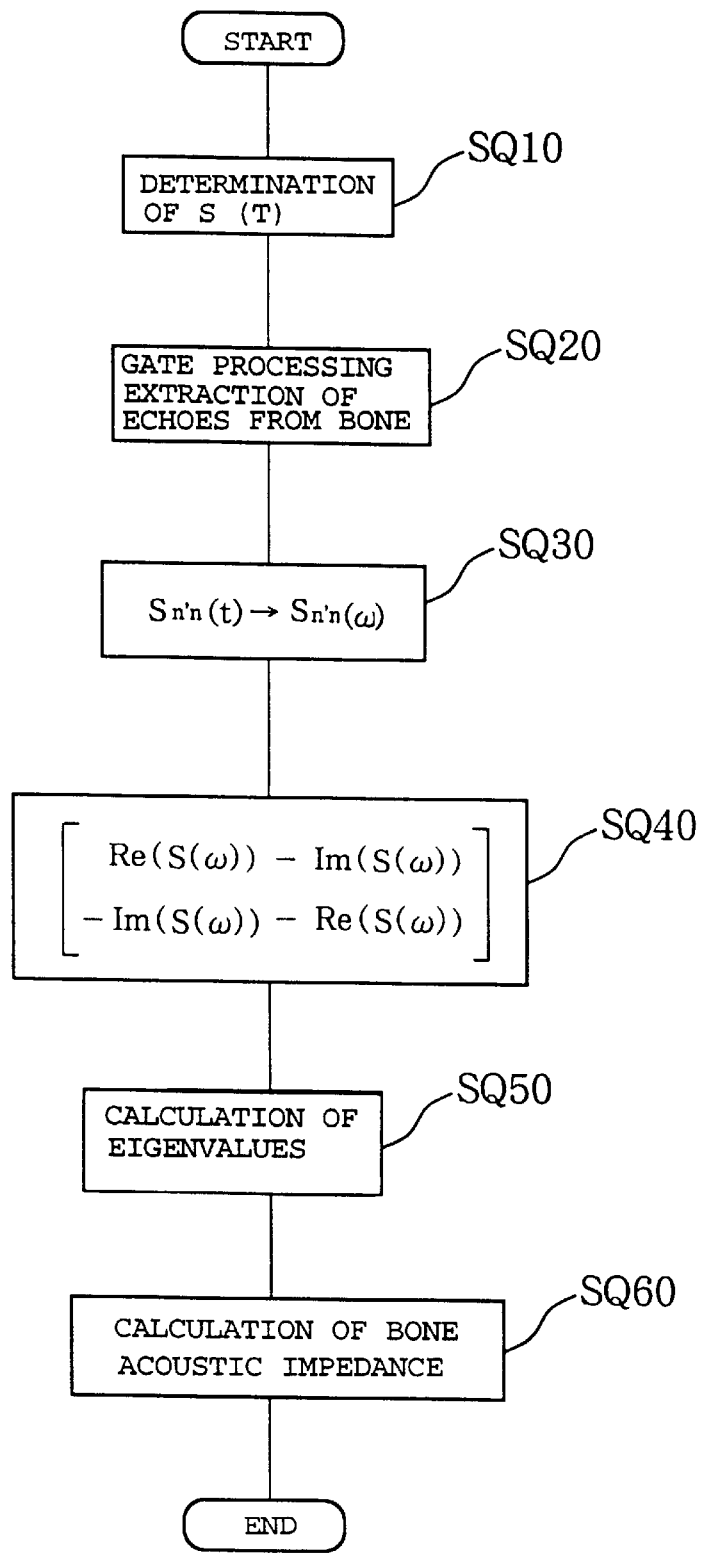
FIG. 10 is a flow chart showing the operating and processing procedure of this embodiment.

The operation of this embodiment (processing flow) will next be explained, with reference to FIG. 10.

Firstly, a bone which is not necessarily flat, but has a sufficiently large radius of curvature relative to the wavelength of the ultrasonic pulses Ai, is selected as the site of measurement. Good sites of measurement include lumbar vertebrae, humerus, tibia, calcaneus or neck of the femur.

On turning the apparatus on after deciding the site of measurement, the CPU initializes all of the components of the apparatus, and then waits for the operator to activate the switch for the start of measurements. At this point, as shown in FIG. 3, the operator smears an ultrasound gel 18 onto the surface (the skin surface X) of the soft tissue Ma covering the bone Mb which is the site of measurement, such as a lumbar vertebra, humerus, tibia, calcaneus or neck of the femur, etc.; he then brings the ultrasonic transducer array 3 into contact with the skin surface X through the ultrasound gel 18, and turns the switch for the start of measurement to ON. On turning the switch for the start of measurement to ON, the CPU 16 executes each of the processes following the processing procedure shown in FIG. 10.

Firstly, in Step SQ10, the CPU determines the waveform S (t), under the control of the subprogram for controlling transmission/reception time. Then it constructs an 8×8 (8 : number of cells) real symmetrical matrix [S (t)].

To do this, the CPU controls repeatedly the alternate transmission of ultrasonic pulses Ai and reception of echo signals Ae, 8×8=64 times. In this $4^{th}$ embodiment, on transmitting an ultrasound pulse Ai from the kth cell, the echo Ae is received by all of the cells, and is input to the respective amplifiers and waveformers and A/D converters and then fed to the CPU.

Then, in Steps SQ20 and SQ30, the received waveforms S (t), in the form of a substantially symmetrical 8×8 matrix, is subjected to Fourier transformation, by applying a gate to the waveforms $S_{n'n}$ (t) considered to be echoes received from the bone. And an 8×8 complex symmetrical scattering matrix $[S_{n'n}(\omega)]$ is constructed. In Step 40, the scattering matrix $[S_{n'n}(\omega)]$ constructed in SQ30 is processed to give the N×N real symmetrical matrix shown in Equation (31). In Step SQ50, the largest eigenvalue (absolute value) $\lambda_0$ from Equation (34) is calculated, and the calculated eigenvalue $\lambda_0$ is multiplied by a proportionality constant to find the reflection coefficient of the bone.

The CPU then goes on the Step SQ60, and calculates the acoustic impedance Zb of the bone Mb, under the control of the subprogram for calculating acoustic impedance of the bone Mb.

Thus, with the constitution of this embodiment, it is necessary to calculate the shape of the bone, as is necessary in Embodiments 1–3, and hence signal treatment is greatly speeded up.

Above, embodiments of this invention have been described in detail by means of drawings; however, the specific constitution thereof is not restricted to these embodiments, and this invention also includes modifications in design which come within the range of the claims of this invention. For example, the ultrasonic wave vibrator elements constituting the transducers is not restricted to the thick oscillating type, but can be of the flexible oscillating type.

Similarly, there is no restriction as to the central frequency employed. The number of cells is not restricted to 64 or 256, but can be increased or decreased as required. In addition, the ultrasonic transducers do not need to be in a 2-dimensional array—the transducers can be arranged in a 1-dimensional linear pattern.

Moreover, since the acoustic impedance of soft tissue Ma is close to the acoustic impedance of water, the acoustic impedance of water (known) can be used instead of the acoustic impedance of the soft tissue Ma in Equation (12) to Equation (15).

Figure 11:
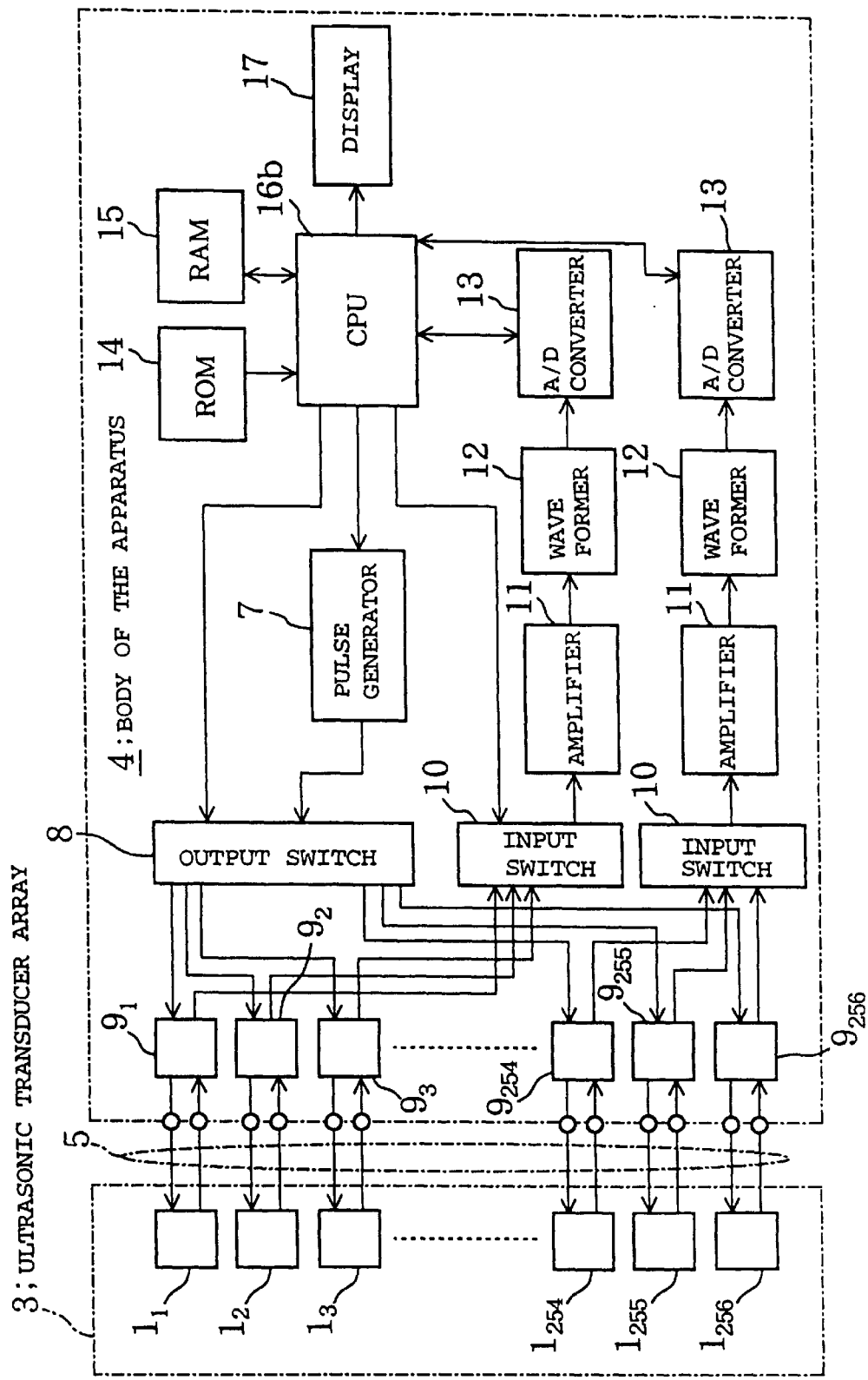
FIG. 11 is a block diagram showing the electrical components of an ultrasonic pulse-echo apparatus for diagnosing osteoporosis which is a different modification of the 1$^{st}$ embodiment.

In passing, the cells $1_1, 1_2, \ldots, 1_N$ can be divided into several groups, with an A/D converter 13, 13 being used for each group, as shown in FIG. 11.

Also, in Embodiment 1 above N×N pulses (where N is the number of cells) are generated; however, from the reciprocity theorem the lower limit is N (N+1)/2.

It should also be noted that it is not necessary to use the highest single eigenvalue: several eigenvalues counted from the absolute highest value can be used.

INDUSTRIAL APPLICABILITY

The ultrasonic pulse-echo apparatus and method of the present invention for diagnosing osteoporosis is suitable for placing in hospitals, sports facilities and health and welfare facilities, etc.; and the fact that the apparatus small and lightweight, and operation is also simple and there is no danger of exposure to radiation, make it highly desirable as a piece of apparatus for health management in old people's homes.

What is claimed is:

1. an apparatus for diagnosing osteoporosis of a bone including an ultrasonic transducer array comprising a 2-dimensional arrangement or 1-dimensional arrangement of n ultrasonic transducer elements (where n is a natural number $\geq 2$), and means for transmitting and receiving ultrasonic waves, connected to each of the ultrasonic transducer elements, and an A/D converter, which digitalizes signals received from each of said ultrasonic transducer elements, and means for determining echo waveforms, which determines the waveforms $S_{ij}$ (t) of the echo received by the ith ultrasonic transducer element of said N ultrasonic transducer elements from the bone due to the emission of an ultrasonic pulse from the jth ultrasonic transducer element, and means for constructing a scattering matrix, which combines these measurement as necessary to find an N×N scattering matrix $[S_{ij}$ (t)], and fourier transformation means which subjects the scattering matrix $[S_{ij}$ (t)] to a Fourier transformation with time, and means for calculating wave reflection information, which calculates information on wave reflection by the bone on the basis of the Fourier transformed scattering matrix $[S_{ij}(\omega)]$.

2. The apparatus for diagnosing osteoporosis as defined in claim 1, characterized in that the number of combinations used in said means for constructing a scattering matrix is in the range N (N+1)/2 to N×N.

3. The apparatus for diagnosing osteoporosis as defined in claim 1, characterized in that said Fourier transformation means performs a Fourier transformation, base upon an algorithm, by applying a gate to waveforms considered to be echo signals received from the bone.

4. The apparatus for diagnosing osteoporosis as defined in claim 1, 2 or 3, characterized in that said means for calculating wave reflection information calculates information on-wave reflection by the bone, based upon an algorithm, by finding one or several value(s) of λ, counting from the largest absolute value of λ established by Equation (1), and uses the value(s) of λ thus found as the basis for the calculation.

$$\sum_j S_{ij}(\omega)\Psi_j(\omega) = \lambda \Psi_i^*(\omega) \quad (1)$$

$S_{ij}(\omega)$ : Elembents of said scattering matrix $[S_{ij}(\omega)]$ $\Psi_j(\omega)$ : The signal emitted towards the bone from the jth ultrasonic transducer element $\Psi_i^*(\omega)$ : Complex conjugate of $\Psi_i(\omega)$ $\Psi_j(\omega)$ is for standardizing.

5. The apparatus for diagnosing osteoporosis as defined in claim 1, 2 or 3, characterized in that said means for calculating wave reflection information calculates information on wave reflection by the bone of the patient, based upon an algorithm, by calculating one or more eigenvalue(s) λ, counting from the largest absolute eigenvalue λ established by Equation (2), and uses the eigenvalue(s) λ thus found as the basis for the calculation.

$$\begin{bmatrix} Re(S(\omega)) - Im(S(\omega)) \\ -Im(S(\omega)) - Re(S(\omega)) \end{bmatrix} \begin{bmatrix} Re(\vec{\Psi}_{in}(\omega)) \\ Im(\vec{\Psi}_{in}(\omega)) \end{bmatrix} = \lambda \begin{bmatrix} Re(\vec{\Psi}_{in}(\omega)) \\ Im(\vec{\Psi}_{in}(\omega)) \end{bmatrix} \quad (2)$$

Writing Equation (1) in matrix form gives $$S(\omega)\vec{\Psi}_{in}(\omega) = \lambda \vec{\Psi}_{in}^*(\omega)$$

$$S_\omega = \begin{bmatrix} S_{(\omega,0,0)} & S_{(\omega,0,1)} & \cdots & S_{(\omega,0,N-1)} \\ S_{(\omega,1,0)} & & & S_{(\omega,1,N-1)} \\ \vdots & & & \vdots \\ S_{(\omega,N-1,0)} & \cdots & \cdots & S_{(\omega,N-1,N-1)} \end{bmatrix}$$

$$\vec{\Psi}_{in}(\omega) = \begin{bmatrix} \Psi_{in(\omega,0)} \\ \Psi_{in(\omega,1)} \\ \vdots \\ \Psi_{in(\omega,N-1)} \end{bmatrix}$$

S (ω) is a complex symmetrical matrix; when this is written in the form of a matrix separating the real and imaginary parts it reduces to Equation (2). Therefore, λ in Equation (2) is eigenvalues of the real symmetrical matrix $$\begin{bmatrix} ReS(\omega) & -ImS(\omega) \\ -ImS(\omega) & -ReS(\omega) \end{bmatrix}.$$

6. The apparatus for diagnosing osteoporosis of the bone as defined in claim 4 or 5, characterized in that said means for calculating wave reflection information finds the reflection coefficient of the bone, based upon an algorithm, by multiplying said value(s) of λ or eigen-value(s) λ by a proportionality constant.

7. The apparatus for diagnosing osteoporosis as defined in claim 1, characterized in that said means for calculating wave reflection information calculates information on wave reflection by said bone when treated as a planewave problem, based upon a processing algorithm, by finding coordinates of N bone elements (the same number as for said ultrasonic transducer elements) on the basis of the waveforms $S_{ij}$ (t) of said received echo signals, and processing the data in such a way as to reduce reflection of waves from the predetermined waveforms as a planewave problem.

8. The apparatus for diagnosing osteoporosis as defined in claim 7, characterized in that the information on wave reflection by said bone calculated by said means for calculating wave reflection information includes information on wave reflection from cortical bone to the soft tissue, and information on wave reflection from cancellous bone to cortical bone.

9. The apparatus for diagnosing osteoporosis as defined in any one of claims 1, 2 or 3, characterized in that there is a means for calculating bone acoustic impedance, which calculates the acoustic impedance of said bone, or the acoustic impedance of cortical bone and the acoustic impedance of cancellous bone, based on said information on bone wave reflection calculated by said means for calculating information on bone wave reflection.

10. The apparatus for diagnosing osteoporosis as defined in any one of claims 1, 2 or 3, characterized in that it is provided with a pulse generating means which repeatedly generates electrical pulses in a predetermined cycle, and an output switching means in order to be able to connect said pulse generating means 1-1 to any selected 1 of said ultrasonic transducer elements, and to be able to switch over the connection, and an input switching means in order to be able to connect said analogue/digital converter 1-1 to any selected 1 of said ultrasonic transducer elements, and to be able to switch over the connection, and a control means which controls said output switching means so that said electrical pulses produced in said pulse generating means are fed in sequence to each of said ultrasonic transducer elements, and also controls said input switching means so that said received signals output from each of said ultrasonic transducer elements are introduced in sequence to said analogue/digital converter.

11. The apparatus for diagnosing osteoporosis on the bone, as defined in claim 1, 2 or 3, characterized in that it is provided with a pulse generating means which repeatedly generates electrical pulses in a predetermined cycle, and an output switching means in order to be able to connect said pulse generating means 1-1 to any selected 1 of said ultrasonic transducer elements, and to be able to switch over the connection, and an input switching means in order to be able to connect said analogue/digital converter 1-1 to any selected 1 of said ultrasonic transducer elements, and to be able to switch over the connection, and a control means which controls said output switching means so that said electrical pulses produced in said pulse generating means are fed in sequence to each of said ultrasonic transducer elements, and also controls said input switching means so that said received signals output from each of said ultrasonic transducer elements are introduced in sequence to said analogue/digital converter, the apparatus being further characterized in that it is provided with an ultrasonic transducer array of N ultrasonic transducer elements (where N is a natural number≧2) arranged in two-dimensions or in one-dimension, and said control means controls said output switching means so that at least N electrical pulses are distributed to each of said ultrasonic transducer elements, and also controls said input switching means in relation to the N echoes from the bone generated by the N ultrasonic pulses emitted in sequence from the aforementioned ultrasonic transducer elements, so that each of said echo signals received from different aforementioned ultrasonic elements are extracted in sequence and introduced to said analogue/digital converter.

12. The apparatus for diagnosing osteoporosis as defined in any one of claims 1, 2 or 3, characterized in that it is provided with an ultrasonic transducer array which has a total of A×B ultrasonic transducer elements divided into B groups with A in each (where B and B are natural numbers ≧2), and a pulse generating means which repeatedly generates electrical pulses in a determined cycle, and B aforementioned analogue/digital converters, one for each group, and an output switching means in order to enable any 1 selected aforementioned ultrasonic transducer element to be connected 1-1 to said pulse generating means, and to be able to switch the connection, and an input switching means in order to enable any 1 selected aforementioned ultrasonic transducer element in each group to be connected 1-1 to said analogue/digital converter, and to be able to switch the connections, and a control means which controls said output switching means so that at least A electrical pulses are distributed to each of said ultrasonic transducer elements, and also controls said input switching means in relation to the A echoes from the bone generated in response to A ultrasonic pulses emitted in sequence from the same aforementioned ultrasonic transducer elements, so that aforementioned echo signals received from different aforementioned ultrasonic transducer elements in each group are sequentially extracted and introduced to the corresponding analogue/digital converter.

13. The apparatus for diagnosing osteoporosis as defined in any one of claims 1, 2 or 3, characterized in that it is provided with a plurality of aforementioned analogue/digital converters connected 1-1 with each of said ultrasonic transducer elements, and a pulse generating means which generates electrical pulses repeatedly in a determined cycle, and an output switching means in order to enable the selection or switching of any of said ultrasonic transducer elements connected 1-1 to the said pulse generating means, and a control means which controls said output control means so that electrical pulses produced in said pulse generating means are fed in sequence to each of said ultrasonic transducer elements.

14. The apparatus for diagnosing osteoporosis as defined in any of claims 1–8, characterized in that it is provided with a plurality of aforementioned analogue/digital converters connected 1-1 with each of said ultrasonic transducer elements, and a plurality of pulse generating means connected 1-1 with each of said ultrasonic transducer elements, and a control means which feeds electrical pulses sequentially to each of the ultrasonic transducer elements.

15. The apparatus for diagnosing osteoporosis in which ultrasonic pulses are emitted in sequence from an array of ultrasonic transducers, which is an apparatus for diagnosing osteoporosis in which a set number of times, ultrasonic pulses are emitted in sequence from each of the transducer elements of an array of ultrasonic transducers comprising a plurality of ultrasonic transducer elements arranged in two-dimensions or one-dimension, in contact with the surface of the skin of the examinee covering a predetermined bone, in the direction of a predetermined area of said bone, and the echoes generated from said bone for each pulse that is emitted are received by the ultrasonic transducer elements above, and osteoporosis is diagnosed by predetermined analysis of predetermined received signals after converting the latter into digital echo signals by means of an analogue/digital converter, characterized in that it has the capability of outputting ultrasonic waves of a waveform represented by Equation (3) from said plurality of ultrasonic transducer elements to predetermined areas of said bone in the site of measurement;

$$\begin{bmatrix} a_{1(t)} \\ \vdots \\ a_{N(t)} \end{bmatrix} = F^{-1}\left[ T_{(\omega)}^{-1} \begin{bmatrix} 1 \\ \vdots \\ 1 \end{bmatrix} \right] \quad (3)$$

where $a_1, a_2, \ldots, a_n$ are the waves emitted from the 1st, 2nd, ..., Nth ultrasonic transducer elements, $F^{-1}$ represents a inverse Fourier transformation, $T(\omega)^{-1}$ is an inverse matrix from matrix $T(\omega)$ in which the elements are Green functions including as variables the distances from any given bone element to any given cell.

16. The apparatus for diagnosing osteoporosis of the bone as defined in any one of claims 1, 2 or 3, characterized in that said bone of the measurement site is a lumbar vertebra, humerus, tibia, calcanaeus or neck of the femur.

17. A method for diagnosing osteoporosis characterized in that an ultrasonic transducer array comprising a two dimensional arrangement or one dimensional arrangement of N ultrasonic transducer elements (where N is a natural number ≧2), and means for transmitting and receiving ultrasonic waves, connected to each of the ultrasonic transducer elements, and an A/D converter, which digitalizes signals received from each of said ultrasonic transducer elements, are used, and the waveforms $S_{ij}(t)$ of the echoes received by the ith ultrasonic transducer elements of said N ultrasonic transducer elements from the bone due to the emission of an ultrasonic pulse from the jth ultrasonic transducer elements are calculated, and these measurements are combined as necessary to find an N×N scattering matrix $[S_{ij}(t)]$, and the scattering matrix $[S_{ij}(t)]$ is subjected to Fourier transformation with time, and information on wave reflection by the bone is calculated on the basis of the Fourier transformed scattering matrix $[S_{ij}(\omega)]$.

18. The method for diagnosing osteoporosis as defined in claim 17, characterized in that said wave reflection information is calculated by finding one or several value(s) of λ, counting from the largest absolute value of λ established by Equation (4), and using the value(s) of λ thus found as the basis for the calculation.

$$\sum_j S_{ij}(\omega)\Psi_j(\omega) = \lambda \Psi_i^*(\omega) \quad (4)$$

$S_{ij}(\omega)$ : Elements of said scattering matrix $[S_{ij}(\omega)]$ $\Psi_j(\omega)$ : The signal emitted towards the bone from the jth ultrasonic transducer element $\Psi_i^*(\omega)$ : Complex conjugate of $\Psi_i(\omega)$ $\Psi_j(\omega)$ is for standardizing.

19. The method for diagnosing osteoporosis as defined in claim 17, characterized in that said wave reflection information is calculated by calculating one or more eigenvalue (s) λ, counting from the largest absolute eigenvalue λ established by Equation (5), and using the eigenvalue(s) λ thus found as the basis for the calculation.

$$\begin{bmatrix} Re(S(\omega)) - Im(S(\omega)) \\ -Im(S(\omega)) - Re(S(\omega)) \end{bmatrix} \begin{bmatrix} Re(\vec{\Psi}_{in}(\omega)) \\ Im(\vec{\Psi}_{in}(\omega)) \end{bmatrix} = \lambda \begin{bmatrix} Re(\vec{\Psi}_{in}(\omega)) \\ Im(\vec{\Psi}_{in}(\omega)) \end{bmatrix} \quad (5)$$

Writing Equation (4) [sic] in matrix form gives $$S(\omega)\vec{\Psi}_{in}(\omega) = \lambda \vec{\Psi}_{in}^*(\omega)$$

$$S_\omega = \begin{bmatrix} S_{(\omega,0,0)} & S_{(\omega,0,1)} & \cdots & S_{(\omega,0,N-1)} \\ S_{(\omega,1,0)} & & & S_{(\omega,1,N-1)} \\ \vdots & & & \vdots \\ S_{(\omega,N-1,0)} & \cdots & \cdots & S_{(\omega,N-1,N-1)} \end{bmatrix}$$

$$\vec{\Psi}_{in}(\omega) = \begin{bmatrix} \Psi_{in(\omega,0)} \\ \Psi_{in(\omega,1)} \\ \vdots \\ \Psi_{in(\omega,N-1)} \end{bmatrix}.$$

20. The method for diagnosing osteoporosis as defined in claim 17, characterized in that information on wave reflection by said bone is calculated after reduction to a planewave problem, by processing the data in such a way as to reduce wave reflection from the predetermined shape to a planewave problem.

21. The method for diagnosing osteoporosis in which ultrasonic pulses are emitted in sequence from an array of ultrasonic transducers, which is a method for diagnosing osteoporosis in which a set number of times, ultrasonic pulses are emitted in sequence from each of the transducer elements of an array of ultrasonic transducers comprising a plurality of ultrasonic transducer elements arranged in two-dimensions or one-dimension, in contact with the surface of the skin covering a predetermined bone, in the direction of a predetermined area said bone, and the echoes generated from said bone for each pulse that is emitted are received by said ultrasonic transducer elements, and osteoporosis is diagnosed by predetermined analytical processing of predetermined received signals after converting the latter into digital echo signals by means of an analogue/digital converter, characterized in that ultrasonic waves of the waveform represented by Equation (6) are output from said plurality of ultrasonic transducer elements to the predetermined area of the bone above which is the site of measurement;

$$\begin{bmatrix} a_1(t) \\ \vdots \\ a_{N(t)} \end{bmatrix} = F^{-1} \begin{bmatrix} T_{(\omega)}^{-1} \begin{bmatrix} 1 \\ \vdots \\ 1 \end{bmatrix} \end{bmatrix} \quad (6)$$

where $a_1, a_2, \ldots, a_n$ are the waves emitted from the 1st, 2nd, ..., Nth ultrasonic transducer elements, $F^{-1}$ represents a inverse Fourier transformation, $T(\omega)^{-1}$ is an inverse matrix from matrix $T(\omega)$ in which the elements are Green functions including as functions the distances between any bone element to any cell.

* * * * *